United States Patent [19]

Marchington et al.

[11] Patent Number: 4,518,415
[45] Date of Patent: May 21, 1985

[54] 1-(TETRAHYDROFURYLMETHYL)AZOLES

[75] Inventors: Anthony F. Marchington, Reading; Timothy Lewis, Maidenhead; John M. Clough, Buckinghamshire; Paul A. Worthington, Maidenhead; John Dalziel, Berkshire, all of England

[73] Assignee: Imperial Chemical Industries PLC, London, England

[21] Appl. No.: 459,966

[22] Filed: Jan. 21, 1983

[30] Foreign Application Priority Data

Feb. 9, 1982 [GB] United Kingdom ............ 8203707
Apr. 19, 1982 [GB] United Kingdom ............ 8211290
May 11, 1982 [GB] United Kingdom ............ 8213652
Nov. 2, 1982 [GB] United Kingdom ............ 8231263

[51] Int. Cl.³ ............ A01N 43/50; A01N 43/64; C07D 405/06; C07F 1/00
[52] U.S. Cl. ............ 71/92; 71/76; 71/18; 548/101; 548/262; 548/336; 549/369; 549/374; 549/504; 549/560; 560/51; 560/60; 560/104; 568/425; 568/812; 514/184; 514/383
[58] Field of Search ............ 548/101, 262, 336; 424/245, 269, 273 R; 71/92, 76, 78

[56] References Cited

U.S. PATENT DOCUMENTS 4,079,062 3/1978 Van Reet ............... 424/269
4,160,838 7/1979 Van Reet ............... 424/269
4,289,526 9/1981 de Fraine et al. ........ 424/269

FOREIGN PATENT DOCUMENTS 0003560 8/1979 European Pat. Off. ........ 548/336
0044276 1/1982 European Pat. Off. ........ 262/
2903653 8/1979 Fed. Rep. of Germany .

Primary Examiner—Alton D. Rollins
Attorney, Agent, or Firm—Cushman, Darby & Cushman

[57] ABSTRACT

Compounds useful as plant growth regulators and fungicides and having the formula

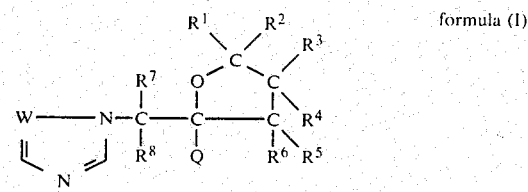

formula (I)

and stereoisomers thereof, wherein W is —CH= or =N—; Q is optionally substituted aryl, especially optionally substituted phenyl, or optionally substituted aralkyl or alkyl; $R^1$, $R^2$, $R^3$, $R^4$, $R^5$ and $R^6$, which may be the same or different, are H, optionally substituted alkyl, cycloalkyl, aralkyl or phenyl; $R^7$ and $R^8$ are H, alkyl or optionally substituted phenyl; and acid addition salts and metal complexes thereof, and processes and intermediates for their preparation.

6 Claims, No Drawings

1-(TETRAHYDROFURYLMETHYL)AZOLES

This invention relates to triazole and imidazole compounds useful as fungicides, to processes for preparing them, to fungicidal compositions containing them, and to methods of using them to combat fungi, especially fungal infections in plants, and to regulate plant growth.

The invention provides a compound having the general formula (I):

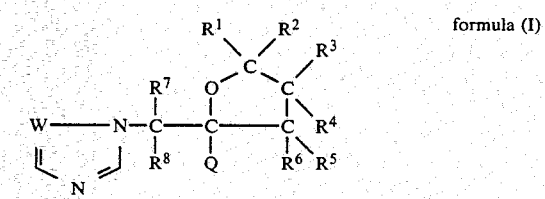

formula (I)

and stereoisomers thereof, wherein W is —CH= or =N—; Q is optionally substituted aryl, especially optionally substituted phenyl, or optionally substituted aralkyl or alkyl; $R^1$, $R^2$, $R^3$, $R^4$, $R^5$ and $R^6$, which may be the same or different, are H, optionally substituted alkyl, cycloalkyl, aralkyl or phenyl; $R^7$ and $R^8$ are H, alkyl or optionally substituted phenyl; and acid addition salts and metal complexes thereof. Preferred alkyl groups contain from 1 to 6, especially 1 to 4, carbon atoms. Preferred cycloalkyl groups are cyclopropyl, cyclobutyl, cyclopentyl and cyclohexyl. The "alkyl" moiety in aralkyl preferably contains from 1 to 4 carbon atoms.

The compounds of the invention contain at least one chiral centre. Such compounds are generally obtained in the form of racemic mixtures. However, these and other mixtures can be separated into the individual isomers by methods known in the art and this invention embraces such isomers.

Examples of suitable substituent groups for Q, $R^1$, $R^2$, $R^3$, $R^4$, $R^5$, $R^6$, $R^7$ and $R^8$ when they represent aralkyl or aryl, especially benzyl or phenyl, are halogen, haloalkyl, alkyl, alkoxy (especially containing 1 to 4 carbon atoms), cyano, nitro, optionally substituted phenyl and optionally substituted phenoxy. Cyano and nitro are less preferred substituents. Phenyl is preferred to benzyl.

Suitably the aryl, especially phenyl, is unsubstituted or substituted with 1, 2 or 3 ring substituents, which may be the same or different, as defined above. Examples of Q, $R^1$, $R^2$, $R^3$, $R^4$, $R^5$, $R^6$, $R^7$ and $R^8$ are phenyl, 2-, 3- or 4-chlorophenyl, 2,4- or 2,6-dichlorophenyl, 2,4- or 2,6-difluorophenyl, 2-, 3- or 4-fluorophenyl, 2-, 3- or 4-bromophenyl, 2-, 3- or 4-methoxyphenyl, 2,4-dimethoxyphenyl, 2-, 3- or 4-ethoxyphenyl, 2-fluoro-4-chlorophenyl, 2-chloro-4-fluorophenyl, 2-, 3- or 4-methylphenyl, 2-, 3- or 4-ethylphenyl, 2-, 3- or 4-trifluoromethylphenyl, 4-phenylphenyl (4-biphenylyl), 2-chloro-4-methoxyphenyl, 2-fluoro-4-methoxyphenyl, 2-chloro-4-methylphenyl and 2-fluoro-4-methylphenyl, 4-isopropylphenyl, 2-methyl-4-chlorophenyl or 2-methyl-4-fluorophenyl.

When Q, $R^1$, $R^2$, $R^3$, $R^4$, $R^5$, $R^6$, $R^7$ or $R^8$ is alkyl it can be a straight or branched chain alkyl group having 1 to 6, eg. 1 to 4 carbon atoms; examples are methyl, ethyl, propyl (n- or iso-propyl) and butyl (n-, sec-, iso- or t-butyl). Q is preferably t-butyl. Suitable substituents for $R^1$ to $R^6$ when these are alkyl groups include halogen, alkoxy and hydroxy. A preferred haloalkyl group is $CF_3$.

The moiety W is preferably =N—, ie. the preferred compounds are triazoles.

The salts can be salts with inorganic or organic acids eg. hydrochloric, nitric, sulphuric, acetic, 4-toluenesulphonic or oxalic acid.

Suitably the metal complex is one including, as the metal, copper, zinc, manganese or iron. It preferably has the formula:

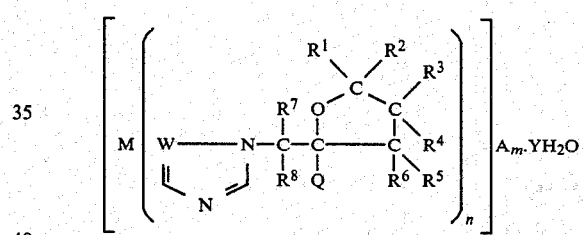

wherein W, Q, $R^1$, $R^2$, $R^3$, $R^4$, $R^5$, $R^6$, $R^7$ and $R^8$ are as defined above, M is a metal, A is an anion (eg. a chloride, bromide, iodide, nitrate, sulphate or phosphate anion), n is 2 or 4, y is 0 or an integer of 1 to 12, and m is integer consistent with valency.

Examples of the compounds of the invention are shown in Table I.

TABLE I

| COMPOUND NUMBER | Q | W | $R^1$ | $R^2$ | $R^3$ | $R^4$ | $R^5$ | $R^6$ | $R^7$ | $R^8$ | MELTING POINT °C. |
|---|---|---|---|---|---|---|---|---|---|---|---|
| 1 | 4-Cl—$C_6H_4$ | N | H | H | H | H | H | H | H | H | Oil |
| 2 | 4-Cl—$C_6H_4$ | CH | H | H | H | H | H | H | H | H | Oil |
| 3 | 4-Cl—$C_6H_4$ | N | H | H | H | H | n-$C_3H_7$ | H | H | H | Oil* |
| 4 | 4-Cl—$C_6H_4$ | N | H | H | n-$C_3H_7$ | H | H | H | H | H | 47–50* |
| 5 | 4-Cl—$C_6H_4$ | N | H | H | H | H | $C_2H_5$ | H | H | H | 100–105* |
| 6 | 4-Cl—$C_6H_4$ | N | $CH_3$ | $CH_3$ | H | H | H | H | H | H | 79–80 |
| 7 | 4-Cl—$C_6H_4$ | CH | $CH_3$ | $CH_3$ | H | H | H | H | H | H | 62–65 |
| 8 | 4-Cl—$C_6H_4$ | N | H | H | $C_2H_5$ | H | H | H | H | H | Oil* |
| 9 | 2,4-di-Cl—$C_6H_3$ | N | n-$C_3H_7$ | H | H | H | H | H | H | H | 83–84$^A$ |
| 10 | 2,4-di-Cl—$C_6H_3$ | N | n-$C_3H_7$ | H | H | H | H | H | H | H | 52–54$^B$ |
| 11 | 4-Cl—$C_6H_4$ | N | $C_2H_5$ | $C_2H_5$ | H | H | H | H | H | H | 82–83 |
| 12 | 4-Cl—$C_6H_4$ | N | n-$C_3H_7$ | n-$C_3H_7$ | H | H | H | H | H | H | Oil |
| 13 | 4-Cl—$C_6H_4$ | N | H | H | $CH_3$ | H | H | H | H | H | 46–50* |
| 14 | 4-Cl—$C_6H_4$ | N | H | H | H | H | $CH_3$ | H | H | H | 82–83* |
| 15 | 4-Cl—$C_6H_4$ | N | n-$C_3H_7$ | H | H | H | H | H | H | H | 55–61$^A$ |
| 16 | 4-Cl—$C_6H_4$ | N | n-$C_3H_7$ | H | H | H | H | H | H | H | 66–67$^B$ |
| 17 | 2,4-di-Cl—$C_6H_3$ | N | H | H | n-$C_3H_7$ | H | H | H | H | H | Oil |
| 18 | 2,4-di-Cl—$C_6H_3$ | N | H | H | H | H | H | H | H | H | 106–107 |
| 19 | 3-F—$C_6H_4$ | N | $CH_3$ | $CH_3$ | H | H | H | H | H | H | 90–91 |
| 20 | 3-F—$C_6H_4$ | N | $C_2H_5$ | $C_2H_5$ | H | H | H | H | H | H | 85–86 |

TABLE I-continued

| COMPOUND NUMBER | Q | W | R¹ | R² | R³ | R⁴ | R⁵ | R⁶ | R⁷ | R⁸ | MELTING POINT °C. |
|---|---|---|---|---|---|---|---|---|---|---|---|
| 21 | 4-F—C₆H₄ | N | CH₃ | CH₃ | H | H | H | H | H | H | 60-61 |
| 22 | 3-Cl—C₆H₄ | N | CH₃ | CH₃ | H | H | H | H | H | H | 79-81 |
| 23 | 3-Cl—C₆H₄ | N | C₂H₅ | C₂H₅ | H | H | H | H | H | H | 65-67 |
| 24 | 4-Cl—C₆H₄ | N | CH₃ | H | H | H | H | H | H | H | 81-83ᴬ |
| 25 | 4-Cl—C₆H₄ | N | CH₃ | H | H | H | H | H | H | H | Oilᴮ |
| 26 | 4-Cl—C₆H₄ | N | C₂H₅ | H | H | H | H | H | H | H | 48-53ᴬ |
| 27 | 4-Cl—C₆H₄ | N | C₂H₅ | H | H | H | H | H | H | H | Oilᴮ |
| 28 | 4-Cl—C₆H₄ | N | CH₃ | C₂H₅ | H | H | H | H | H | H | 53-58* |
| 29 | 4-Cl—C₆H₄ | N | CH₃ | n-C₃H₇ | H | H | H | H | H | H | Oilᴬ |
| 30 | 4-Cl—C₆H₄ | N | CH₃ | n-C₃H₇ | H | H | H | H | H | H | 47-50ᴮ |
| 31 | 4-Cl—C₆H₄ | N | CH₃ | n-C₄H₉ | H | H | H | H | H | H | Oilᴬ |
| 32 | 4-Cl—C₆H₄ | N | CH₃ | n-C₄H₉ | H | H | H | H | H | H | 52-58ᴮ |
| 33 | 4-Cl—C₆H₄ | N | n-C₄H₉ | H | H | H | H | H | H | H | Oilᴬ |
| 34 | 4-Cl—C₆H₄ | N | n-C₄H₉ | H | H | H | H | H | H | H | Oilᴮ |
| 35 | 4-Cl—C₆H₄ | N | CH₃ | CH₃ | H | H | CH₃ | H | H | H | Oilᴬ |
| 36 | 4-Cl—C₆H₄ | N | CH₃ | CH₃ | H | H | CH₃ | H | H | H | 171-173ᴮ |
| 37 | 4-Cl—C₆H₄ | CH | CH₃ | CH₃ | H | H | CH₃ | H | H | H | 180-182ᴬ |
| 38 | 4-Cl—C₆H₄ | CH | CH₃ | CH₃ | H | H | CH₃ | H | H | H | Oilᴮ |
| 39 | 4-Cl—C₆H₄ | N | C₂H₅ | C₂H₅ | H | H | CH₃ | H | H | H | Oil* |
| 40 | 4-Cl—C₆H₄ | CH | C₂H₅ | C₂H₅ | H | H | CH₃ | H | H | H | Oil* |
| 41 | 4-Cl—C₆H₄ | N | CH₃ | CH₃ | CH₃ | H | H | H | H | H | 104-106* |
| 42 | 4-Cl—C₆H₄ | N | C₂H₅ | C₂H₅ | CH₃ | H | H | H | H | H | 72-74* |
| 43 | 2-F—C₆H₄ | N | CH₃ | H | H | H | H | H | H | H | 71-73ᴬ |
| 44 | 2-F—C₆H₄ | N | CH₃ | H | H | H | H | H | H | H | 69-70ᴮ |
| 45 | 2-F—C₆H₄ | N | CH₃ | C₂H₅ | H | H | H | H | H | H | 66-77* |
| 46 | 2-F—C₆H₄ | N | CH₃ | n-C₃H₇ | H | H | H | H | H | H | 42-46ᴬ |
| 47 | 2-F—C₆H₄ | N | CH₃ | n-C₃H₇ | H | H | H | H | H | H | 74-76ᴮ |
| 48 | 2-F—C₆H₄ | N | CH₃ | CH₃ | H | H | H | H | H | H | 90-94 |
| 49 | 2-Cl—C₆H₄ | N | CH₃ | H | H | H | H | H | H | H | 95-96ᴬ |
| 50 | 2-Cl—C₆H₄ | N | CH₃ | H | H | H | H | H | H | H | Oilᴮ |
| 51 | 2-Cl—C₆H₄ | N | CH₃ | CH₃ | H | H | H | H | H | H | 83-85 |
| 52 | 2-Cl—C₆H₄ | N | CH₃ | C₂H₅ | H | H | H | H | H | H | 48-57* |
| 53 | 2-Cl—C₆H₄ | N | CH₃ | n-C₃H₇ | H | H | H | H | H | H | Oilᴬ |
| 54 | 2-Cl—C₆H₄ | N | CH₃ | n-C₃H₇ | H | H | H | H | H | H | Oilᴮ |
| 55 | 4-Cl—C₆H₄ | N | CH₃ | CH₃ | n-C₃H₇ | H | H | H | H | H | 127-129ᴬ |
| 56 | 4-Cl—C₆H₄ | N | CH₃ | CH₃ | n-C₃H₇ | H | H | H | H | H | 133-114ᴮ |
| 57 | 4-Cl—C₆H₄ | N | C₂H₅ | C₂H₅ | n-C₃H₇ | H | H | H | H | H | Oil* |
| 58 | 2-F,4-Cl—C₆H₃ | N | CH₃ | CH₃ | H | H | H | H | H | H | 81-82 |
| 59 | 2-Cl,4-F—C₆H₃ | N | CH₃ | CH₃ | H | H | H | H | H | H | 96-97 |
| 60 | 4-Cl—C₆H₄ | N | CH₃ | CH₃ | H | H | H | H | CH₃ | H | Oil* |
| 61 | 2,4-di-Cl—C₆H₃ | N | CH₃ | H | H | H | H | H | H | H | Oil* |
| 62 | 4-Cl—C₆H₄ | N | H | H | CH₃ | CH₃ | H | H | H | H | 86-87 |
| 63 | 2,4-di-Cl—C₆H₃ | N | CH₃ | CH₃ | H | H | H | H | H | H | 82-85 |
| 64 | 4-Cl—C₆H₄ | N | H | H | CH₃ | H | CH₃ | H | H | H | |
| 65 | 4-Cl—C₆H₄ | N | CF₃ | H | H | H | H | H | H | H | |
| 66 | 4-Cl—C₆H₄ | N | CH₃ | CH₃ | CH₃ | CH₃ | H | H | H | H | 86-90 |
| 67 | 4-Cl—C₆H₄ | N | H | H | H | H | CH₃ | CH₃ | H | H | |
| 68 | 2,4-di-Cl—C₆H₃ | N | H | H | H | H | CH₃ | CH₃ | H | H | |
| 69 | 4-i-C₃H₇—C₆H₄ | N | CH₃ | CH₃ | H | H | H | H | H | H | 83-84 |
| 70 | 4-CH₃—C₆H₄ | N | CH₃ | CH₃ | H | H | H | H | H | H | 97-98 |
| 71 | 4-C₂H₅—C₆H₄ | N | CH₃ | CH₃ | H | H | H | H | H | H | |
| 72 | 4-CH₃O—C₆H₄ | N | CH₃ | CH₃ | H | H | H | H | H | H | 106-108 |
| 73 | 4-C₂H₅O—C₆H₄ | N | CH₃ | CH₃ | H | H | H | H | H | H | |
| 74 | 2,4-di-F—C₆H₃ | N | CH₃ | CH₃ | H | H | H | H | H | H | |
| 75 | 2-Cl,4-CH₃—C₆H₃ | N | CH₃ | CH₃ | H | H | H | H | H | H | |
| 76 | 2-CH₃,4-Cl—C₆H₃ | N | CH₃ | CH₃ | H | H | H | H | H | H | |
| 77 | 2-F,4-CH₃—C₆H₃ | N | CH₃ | CH₃ | H | H | H | H | H | H | |
| 78 | 2-CH₃,4-F-C₆H₃ | N | CH₃ | CH₃ | H | H | H | H | H | H | |
| 79 | 4-Cl—C₆H₄ | N | i-C₃H₇ | H | H | H | H | H | H | H | |
| 80 | 2,4-di-Cl—C₆H₃ | N | i-C₃H₇ | H | H | H | H | H | H | H | |
| 81 | 2,4-di-Cl—C₆H₃ | N | CH₃ | CH₃ | H | H | H | H | C₆H₅ | H | |
| 82 | 4-Cl—C₆H₄ | N | CH₃ | CH₃ | H | H | H | H | C₆H₅ | H | |
| 83 | 4-CF₃—C₆H₄ | N | CH₃ | CH₃ | H | H | H | H | H | H | |

*mixture of diastereoisomers (NB. Other mixtures of diastereoisomers, as appearing in TABLE II, have different melting points, reflecting the different proportions of the diastereoisomers present).
ᴬdiastereoisomer A
ᴮdiastereoisomer B The compounds of the invention having the general formula (I):

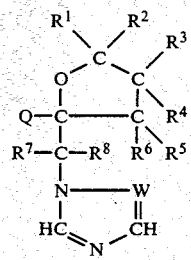

(I)

wherein Q, $R^1$, $R^2$, $R^3$, $R^4$, $R^5$, $R^6$, $R^7$, $R^8$ and W are as defined above, can be prepared by treatment of halides of general formula (II):

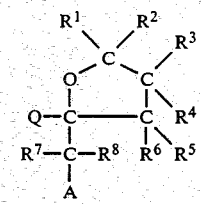

(II)

wherein Q, $R^1$, $R^2$, $R^3$, $R^4$, $R^5$, $R^6$, $R^7$ and $R^8$ are as defined above and A is a halogen (preferably bromine, chlorine or iodine), either with 1,2,4-triazole or with imidazole, each in the presence of an acid-binding agent or in the form of one of its alkali metal salts, in a convenient solvent (such as dimethylformamide or acetonitrile) and at a convenient temperature (such as 60° to 160° C.).

Halides of the general formula (II) can be prepared from olefinic alcohols of general formula (III):

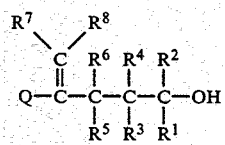

(III)

wherein Q, $R^1$, $R^2$, $R^3$, $R^4$, $R^5$, $R^6$, $R^7$ and $R^8$ are as defined above by treatment with a halogen in a suitable solvent (such as dichloromethane) in the presence of an acid-binding agent (such as pyridine) (see, for example, I. Monkovic, Y. G. Perron, R. Martel, W. J. Simpson and J. A. Gylys, *J. Med. Chem.*, 1973, 16, 403; H.Wong, J. Chapuis and I. Monkobic, *J.Org.Chem.*, 1974, 39, 1042).

Olefinic alcohols of general formula (III) wherein $R^1$ and $R^2$ are both hydrogen can be prepared from olefinic esters of general formula (IV):

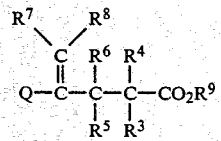

(IV)

wherein $R^3$, $R^4$, $R^5$, $R^6$, $R^7$, $R^8$ and Q are as defined above and $R^9$ is alkyl, alkenyl, alkynyl, optionally-substituted phenyl or aralkyl, by treatment with a reducing agent (such as lithium aluminium hydride) in a suitable solvent (such as diethyl ether or tetrahydrofuran).

Olefinic alcohols of general formula (III) wherein $R^1$ and $R^2$ are the same but are not hydrogen can be prepared by treating olefinic esters of general formula (IV) with Grignard reagents of general formula (V):

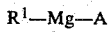

(V)

wherein $R^1$ and A are as defined above, in a suitable solvent (such as diethyl ether or tetrahydrofuran). Grignard reagents of general formula (V) can be prepared by standard methods as set out in the chemical literature.

Alternatively, olefinic alcohols of general formula (III) can be prepared by treatment of carbonyl compounds of general formula (VI):

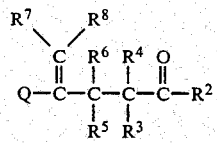

(VI)

wherein $R^2$, $R^3$, $R^4$, $R^5$, $R^6$, $R^7$, $R^8$ and Q are as defined above, with Grignard reagents of general formula (V).

Carbonyl compounds of general formula (VI) wherein $R^2$ is hydrogen can be prepared by selective reduction of olefinic esters of general formula (IV) with, for example, di-isobutylaluminium hydride in a suitable solvent (such as diethyl ether), usually at low temperatures.

Alternatively, carbonyl compounds of general formula (VI) wherein $R^2$ is hydrogen can be prepared by selective oxidation of olefinic alcohols of general formula (III) wherein $R^1$ and $R^2$ are hydrogen with, for example, pyridinium dichromate in a suitable solvent (such as dichloromethane) (see, for example, E. J. Corey and G. Schmidt, *Tetrahedron Letters*, 1979, 399).

Carbonyl compounds of general formula (VI) wherein $R^2$ is not hydrogen can be prepared by oxidation of olefinic alcohols of general formula (III) wherein $R^1$ is hydrogen and $R^2$ is not hydrogen by one of the many oxidation procedures set out in the chemical literature.

Olefinic esters of general formula (IV) can be prepared by olefination of γ-ketoesters of general formula (VII):

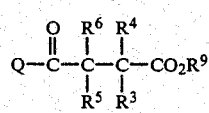

(VII)

wherein $R^3$, $R^4$, $R^6$, $R^9$ and Q are as defined above using, for example, an alkylidenetriphenylphosphorane in a suitable solvent (such as dimethylsulphoxide, diethyl ether, or tetrahydrofuran) (see, for example, R. Greenwald, M. Chaykovsky and E. J. Corey, *J.Org.-Chem.*, 1963, 28, 1128).

γ-Ketoesters of general formula (VII) wherein $R^3$ is hydrogen can be prepared by reaction of aldehydes of general formula (VIII):

Q—CHO     (VIII)

wherein Q is as defined above, with α,β-unsaturated esters of general formula (IX):

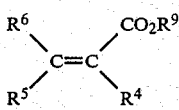
(IX)

wherein $R^4$, $R^5$, $R^6$ and $R^9$ are as defined above, in the presence of cyanide ions or thiazolium salts, in a suitable solvent (such as dimethylformamide or dioxane), or in the absence of a solvent (see, for example, H. Stetter, *Angew. Chem. Int. Edn. English*, 1976, 15, 639).

Aldehydes of general formula (VIII) and $\alpha,\beta$-unsaturated esters of general formula (IX) can be prepared by methods set out in the chemical literature.

Alternatively, carbonyl compounds of general formula (VI) can be prepared by acid-catalysed hydrolysis of acetals/ketals of general formula (X):

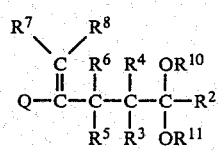
(X)

wherein $R^2$, $R^3$, $R^4$, $R^5$, $R^6$, $R^7$, $R^8$ and Q are as defined above and $R^{10}$ and $R^{11}$ are alkyl, alkenyl or alkynyl, or are joined together to form a ring.

Acetals/ketals of general formula (X) can be prepared by olefination of ketones of general formula (XI):

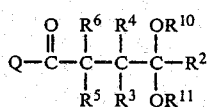
(XI)

wherein $R^2$, $R^3$, $R^4$, $R^5$, $R^6$, $R^{10}$, $R^{11}$ and Q are as defined above using, for example, a suitable alkylidenetriphenylphosphorane in a suitable solvent (such as dimethylsulphoxide, diethyl ether, or tetrahydrofuran) (see, for example, R. Greenwald, M. Chaykovsky and E. J. Corey, *J. Org. Chem.*, 1963, 28, 1128).

Ketones of general formula (XI) can be prepared by oxidation of alcohols of general formula (XII):

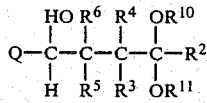
(XII)

wherein $R^2$, $R^3$, $R^4$, $R^5$, $R^6$, $R^{10}$, $R^{11}$ and Q are as defined above using, for example, pyridinium dichromate in dimethylformamide (see, for example, E. J. Corey and G. Schmidt, *Tetrahedron Letters*, 1979, 399).

Alcohols of general formula (XII) can be prepared by reaction of aldehydes of general formula (VIII) with Grignard reagents of general formula (XIII):

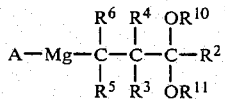
(XIII)

wherein A, $R^2$, $R^3$, $R^4$, $R^5$, $R^{10}$ and $R^{11}$ are as defined above, in a suitable solvent (such as diethyl ether or tetrahydrofuran).

Grignard reagents of general formula (XIII) can be prepared from halides of general formula (XIV):

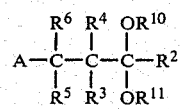
(XIV)

wherein A, $R^2$, $R^3$, $R^4$, $R^5$, $R^6$, $R^{10}$ and $R^{11}$ are as defined above, by standard methods as set out in the chemical literature. The halides of general formula (XIV) can be prepared by methods set out in the chemical literature (see, for example, D. C. Kriesel and O. Gisvold, *J. Pharm. Sci.*, 1971, 60, 1250; J. C. Stowell, *J. Org. Chem.*, 1976, 41, 560; T. Sato, T. Kawara, K. Sakata and T. Fujisawa, *Bull. Chem. Soc. Japan*, 1981, 54, 505).

Alternatively, ketones of general formula (XI) can be prepared by reaction of Grignard reagents of general formula (XIII) with nitriles of general formula (XV):

$$Q\text{—}CN \qquad (XV)$$

wherein Q is as defined above, in a suitable solvent (such as diethyl ether or tetrahydrofuran), followed by hydrolysis and, if required, selective re-acetalisation.

In addition, ketones of general formula (XI) can be prepared by reaction of Grignard reagents of general formula (XIII) with acid halides of general formula (XVI):

(XVI)

wherein Q and A are as defined above, in a suitable solvent (such as diethyl ether or tetrahydrofuran), often at low temperatures (see, for example, T. Sato, T. Kawara, K. Sakata, and T. Fujisawa, *Bull. Chem. Soc. Japan*, 1981, 54, 505).

Nitriles of general formula (XV) and acid halides of general formula (XVI) can be prepared by standard methods set out in the chemical literature.

In an alternative approach, compounds of the invention having the general formula (I) can be prepared by dehydration of 1,4-diols of the general formula (XVII):

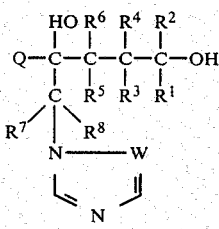
(XVII)

wherein $R^1$, $R^2$, $R^3$, $R^4$, $R^5$, $R^6$, $R^7$, $R^8$, Q and W are as defined above, by one of a number of methods described in the chemical literature [see, for example, H. Kroper, 'Methoden der Organischen Chemie', (Houben-Weyl), 1965, Band VI/3, 528].

Diols of the general formula (XVII) in which $R^1$ and $R^2$ are both hydrogen can be prepared by reduction of either lactones of general formula (XVIII):

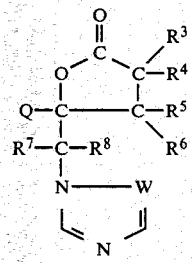

(XVIII)

wherein $R^3$, $R^4$, $R^5$, $R^6$, $R^7$, $R^8$, Q and W are as defined above, or esters of general formula (XIX):

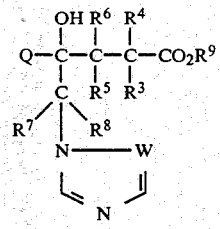

(XIX)

wherein $R^3$, $R^4$, $R^5$, $R^6$, $R^7$, $R^8$, $R^9$, Q and W are as defined above, with a suitable reducing agent (such as lithium aluminium hydride) in a suitable solvent (such as diethyl ether or tetrahydrofuran).

Diols of the general formula (XVII) in which $R^1$ and $R^2$ are the same but are not hydrogen can be prepared by treatment of either the lactone of general formula (XVIII) or the ester of general formula (XIX) with a Grignard reagent of general formula (V) in a suitable solvent (such as diethyl ether or tetrahydrofuran).

Esters of general formula (XIX) can be prepared by treating lactones of the general formula (XVIII) with alcohols of general formula $R^9OH$, wherein $R^9$ is as defined above, under acidic conditions, either in a suitable solvent or with an excess of the alcohol as solvent.

Lactones of the general formula (XVIII) can be prepared by treating epoxides of the general formula (XX):

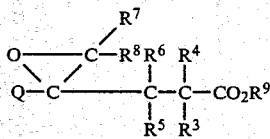

(XX)

wherein $R^3$, $R^4$, $R^5$, $R^6$, $R^7$, $R^8$, $R^9$ and Q are as defined above, either with 1,2,4-triazole or with imidazole, each in the presence of an acid-binding agent or in the form of one of its alkali metal salts, in a convenient solvent (such as dimethylformamide or acetonitrile) and at a suitable temperature (such as 60° to 160° C.).

Epoxides of general formula (XX) in which $R^7$ and $R^8$ are both hydrogen atoms can be prepared by treatment of γ-ketoesters of general formula (VII) with either dimethylsulphonium methylide (see E. J. Corey and M. Chaykovsky, *J. Amer. Chem. Soc.*, 1962, 84, 3782) or dimethyloxosulphonium methylide (see E. J. Corey and M. Chaykovsky, *J. Amer. Chem. Soc.*, 1965, 87, 1353) using methods set out in the chemical literature.

Alternatively, epoxides of general formula (XX) can be prepared by oxidation of olefinic esters of general formula (IV) using, for example, a peracid in a suitable solvent, by methods set out in the chemical literature.

In addition to the methods described earlier, γ-ketoesters of general formula (VII) can be prepared by esterification of acids of general formula (XXI):

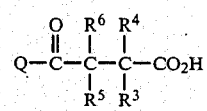

(XXI)

wherein Q, $R^3$, $R^4$, $R^5$ and $R^6$ are as defined above, with alcohols of general formula $R^9OH$, wherein $R^9$ is as defined above.

Acids of general formula (XXI) in which Q is an optionally substituted aryl group can be prepared by reaction between a species QH, wherein Q is an optionally substituted aryl group, and a succinic anhydride of general formula (XXII):

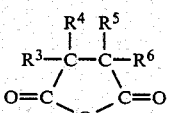

(XXII)

wherein $R^3$, $R^4$, $R^5$ and $R^6$ are as defined above, in the presence of an acid, for example a Lewis acid such as aluminium chloride (see, for example, L. F. Fieser and A. M. Seliqman, *J. Amer. Chem. Soc.*, 1938, 60, 170).

Succinic anhydrides of general formula (XXII) can be prepared by standard methods set out in the chemical literature.

In an alternative approach, the compounds of the invention of general formula (I) in which $R^3$, $R^4$, $R^5$ and $R^6$ are all hydrogen atoms can be prepared from acetylenic diols of general formula (XXIII):

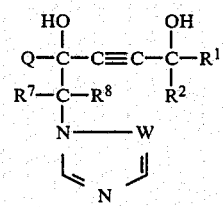

(XXIII)

wherein $R^1$, $R^2$, $R^7$, $R^8$, Q and W are as defined above, by hydrogenation in the presence of a suitable catalyst, for example, palladium on charcoal. Cyclisation with loss of water to give (I) can take place simultaneously under the same reaction conditions (see, for example, R. A. Raphael, "Acetylenic Compounds in Organic Synthesis", Butterworths, 1955, pages 171-2), or may be carried out in a subsequent step by one of a number of methods described in the chemical literature [see, for example, H. Kroper, "Methoden der Organischen Chemie", (Houben-Weyl), 1965, Band VI/3, 528].

Acetylenic diols of the general formula (XXIII) can be prepared by treatment of epoxides of the general formula (XXIV):

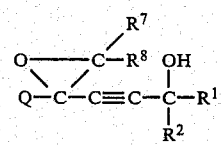

(XXIV)

wherein $R^1$, $R^2$, $R^7$, $R^8$ and Q are as defined above, or halohydrins of general formula (XXV):

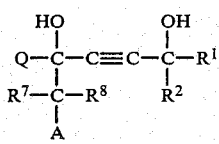

(XXV)

wherein $R^1$, $R^2$, $R^7$, $R^8$, Q and A are as defined above, either with 1,2,4-triazole or with imidazole, each in the presence of an acid-binding agent or in the form of one of its alkali metal salts, in a convenient solvent (such as dimethylformamide or acetonitrile) and at a convenient temperature.

Epoxides of the general formula (XXIV), or halohydrins of the general formula (XXV), or mixtures containing both epoxide (XXIV) and halohydrin (XXV), can be prepared by treatment of a ketone of general formula (XXVI):

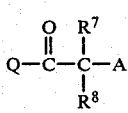

(XXVI)

wherein $R^7$, $R^8$ and A are as defined above, with a metallated acetylene of general formula (XXVII):

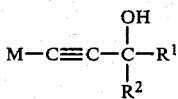

(XXVII)

wherein $R^1$ and $R^2$ are as defined above and M is a metal atom or a combination of a metal atom and one or more halogen atoms, for example lithium or magnesium-A where A is as defined above, in a suitable solvent such as tetrahydrofuran.

Metallated acetylenes of general formula (XXVII) can be prepared by metallation of the parent acetylenes of general formula (XXVIII):

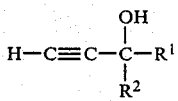

(XXVIII)

wherein $R^1$ and $R^2$ are as defined above, by standard methods set out in the chemical literature. Acetylenes of general formula (XXVIII) and ketones of general formula (XXVI) can be prepared by standard methods set out in the chemical literature.

In a related procedure, halides of general formula (II) can be prepared by hydrogenation of diols of general formula (XXV) in the presence of a suitable catalyst such as palladium on charcoal. Cyclisation with loss of water can take place simultaneously under the same reaction conditions (see, for example, R. A. Raphael, "Acetylenic Compounds in Organic Synthesis", Butterworths, 1955, pages 171-2), or may be carried out in a subsequent step by one of a number of methods described in the chemical literature [see, for example, H. Kroper, "Methoden der Organischen Chemie", (Houben-Weyl), 1965, Band VI/3, 528].

In an alternative approach, olefinic alcohols of general formula (III) can be prepared by treatment of aldehydes or ketones of general formula (XXIX):

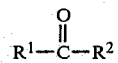

(XXIX)

wherein $R^1$ and $R^2$ are as defined above, with Grignard reagents of general formula (XXX):

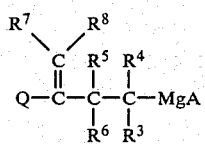

(XXX)

wherein $R^3$, $R^4$, $R^5$, $R^6$, $R^7$, $R^8$, A and Q are as defined above, in a suitable solvent such as diethyl ether or tetrahydrofuran.

The Grignard reagents of general formula (XXX) can be prepared from the corresponding halides of general formula (XXXI):

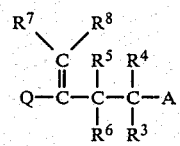

(XXXI)

wherein $R^3$, $R^4$, $R^5$, $R^6$, $R^7$, $R^8$, A and Q are as defined above, by standard methods set out in the chemical literature.

The halides of general formula (XXXI) can be prepared from homoallylic alcohols of general formula (XXXII):

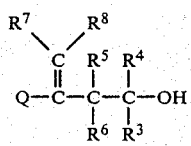

(XXXII)

wherein $R^3$, $R^4$, $R^5$, $R^6$, $R^7$, $R^8$ and Q are as defined above, by standard methods described in the chemical literature. Methods described in the chemical literature can also be used to prepare homoallylic alcohols of general formula (XXXII) (see, for example, B. B. Snider and D. J. Rodini, Tet. Letts., 1980, 21, 1815; A. T. Blomquist and R. J. Himics, J. Org. Chem., 1967, 33, 1156; R. J. Crawford, W. F. Erman and C. D. Broaddus, J. Amer. Chem. Soc., 1972, 94, 4298; S. Akiyama and J. Hooz, Tet. Letts., 1973, 4115) and aldehydes or ketones of general formula (XXIX).

Furthermore, olefinic alcohols of general formula (III) can be prepared by olefination of ketones of general formula (XXXIII):

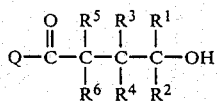

(XXXIII)

wherein $R^1$, $R^2$, $R^3$, $R^4$, $R^5$, $R^6$ and Q are as defined above, using, for example, an alkylidenetriphenylphosphorane in a suitable solvent such as dimethylsulphoxide, diethyl ether, or tetrahydrofuran (see, for example, R. Greenwald, M. Chaykovsky and E. J. Corey, *J. Org Chem.*, 1963, 28, 1128).

Ketones of general formula (XXXIII) can be prepared by acid-catalysed hydrolysis of ketals of general formula (XXXIV):

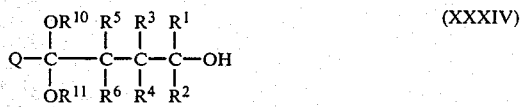

(XXXIV)

wherein $R^1$, $R^2$, $R^3$, $R^4$, $R^5$, $R^6$, $R^{10}$, $R^{11}$ and Q are as defined above, under standard conditions as described in the chemical literature.

Ketals of the general formula (XXXIV) can be prepared by treatment of aldehydes or ketones of general formula (XXIX) with Grignard reagents of general formula (XXXV):

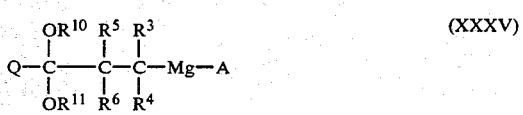

(XXXV)

wherein $R^3$, $R^4$, $R^5$, $R^6$, $R^{10}$, $R^{11}$, Q and A are as defined above, in a suitable solvent such as diethyl ether or tetrahydrofuran.

Grignard reagents of general formula (XXXV) can be made by standard methods from the corresponding halides of general formula (XXXVI):

(XXXVI)

wherein $R^3$, $R^4$, $R^5$, $R^6$, $R^{10}$, $R^{11}$, A and Q are as defined above.

Halides of the general formula (XXXVI) can be prepared by reaction of ketones of general formula (XXXVII):

(XXXVII)

wherein $R^3$, $R^4$, $R^5$, $R^6$, Q and A are as defined above, with alcohols of general formula $R^{10}OH$, or diols (especially ethylene glycol or propan-1,3-diol), under acidic conditions.

Ketones of general formula (XXXVII) can be prepared by standard methods described in the chemical literature. For example, ketones or general formula (XXXVII) in which Q is an optionally substituted phenyl ring can be prepared by reaction between a species QH and an acid halide of general formula (XXXVIII):

(XXXVIII)

wherein $R^3$, $R^4$, $R^5$, $R^6$ and A are as defined above and X is a halogen atom, especially a chlorine or bromine atom, in the presence of an acid, especially a Lewis acid. Acid halides of the general formula (XXXVIII) can be prepared by standard methods.

In another approach, compounds of the general formula (I) in which $R^4$ is a hydrogen atom can be made by acid-catalysed cyclisation of olefinic alcohols of general formula (XXXIX):

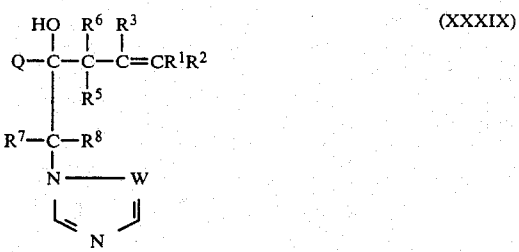

(XXXIX)

wherein $R^1$, $R^2$, $R^3$, $R^5$, $R^6$, $R^7$, $R^8$, Q and W are as defined above.

Similarly, compounds of the general formula (I) in which $R^1$ is equal to the group $-CHR^{12}R^{13}$, wherein $R^{12}$ and $R^{13}$, which may be the same or different, are H, alkyl, cycloalkyl or aralkyl, can be made by acid-catalysed cyclisation of olefinic alcohols of general formula (XXXX):

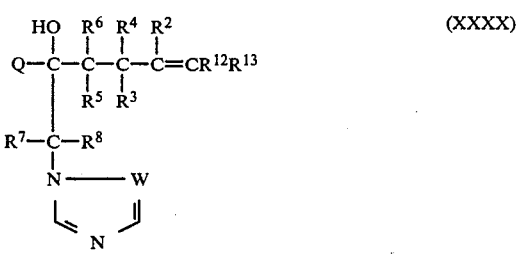

(XXXX)

wherein $R^2$, $R^3$, $R^4$, $R^5$, $R^6$, $R^7$, $R^8$, $R^{12}$, $R^{13}$, W and Q are as defined above.

Analogously, compounds of the general formula (II) in which $R^4$ is a hydrogen atom, or in which $R^1$ is equal to the group $-CHR^{12}R^{13}$, can be made by acid-catalysed cyclisation of olefinic alcohols of general formula (XXXXI):

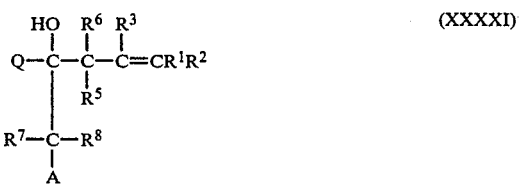

(XXXXI)

wherein $R^1$, $R^2$, $R^3$, $R^5$, $R^6$, $R^7$, $R^8$, A and Q are as defined above, or (XXXXII):

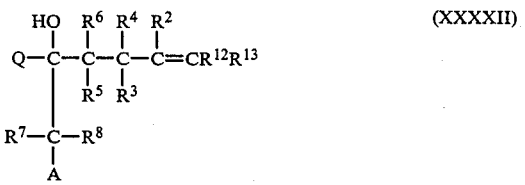

(XXXXII)

wherein $R^2$, $R^3$, $R^4$, $R^5$, $R^6$, $R^7$, $R^8$, $R^{12}$, $R^{13}$, Q and A are as defined above, respectively.

Examples of similar acid-catalysed cyclisations of olefinic alcohols are described in "Methoden der Organischen Chemie", (Houben-Weyl), 1965, Band VI/3, 539.

In another approach, olefinic esters of general formula (IV) can be prepared by heating together an allylic alcohol of general formula (XXXXIII):

(XXXXIII)

wherein $R^5$, $R^6$, $R^7$, $R^8$ and Q are as defined above, with an orthoester of general formula (XXXXIV):

(XXXXIV)

wherein $R^3$, $R^4$ and $R^9$ are as defined above, but $R^9$ is preferably a methyl or ethyl group (see, for example, W. S. Johnson et al., *J. Amer. Chem. Soc.* 1970, 92, 741; R. E. Ireland and D. J. Dawson, *Org. Synth.*, 1975, 54, 74).

Allylic alcohols of general formula (XXXXIII) are available by standard methods (see, for example, M. A. Umbreit and K. B. Sharpless, *J. Amer. Chem. Soc.*, 1977, 99, 5526).

Many of the intermediates described in this discussion [for example, those with general formulae (IV), (VI), (VII), (XI), (XVIII), (XIX), (XX), (XXII) and (XXXIII)] can be elaborated by alkylation, cycloalkylation, alkenylation, alkynylation, or aralkylation using, for example, a base (such as lithium di-isopropylamide) and a halide of general formula $R^1A$, $R^2A$, $R^3A$, $R^4A$, $R^5A$ or $R^6A$, wherein $R^1$, $R^2$, $R^3$, $R^4$, $R^5$, $R^6$, and A are as defined above, or via a suitable enamine, by methods described in the chemical literature (see for example, G. Stork and S. R. Dowd, *J. Amer. Chem. Soc.*, 1963, 85, 2178). For example compounds of general formula (VI) wherein $R^3$ is hydrogen can be converted into compounds of general formula (VI) wherein $R^3$ is alkyl, cycloalkyl, alkenyl, alkynyl or aralkyl by one of these methods.

The compounds, salts and metal complexes are active fungicides, particularly against the diseases:

*Piricularia oryzae* on rice

*Puccinia recondita, Puccinia striiformis* and other rusts on wheat, *Puccinia hodei, Puccinia striiformis* and other rusts on barley, and rusts on other hosts eg. coffee, apples, vegetables and ornamental plants

*Plasmopara viticola* on vines

*Erysiphe graminis* (powdery mildew) on barley and wheat and other powdery mildews on various hosts such as

*Sphaerotheca fuliginea* on cucurbits (eg. cucumber),

*Podosphaera leucotricha* on apples and Uncinula necator on vines

*Helminthosporium* spp. and *Rhynchosporium* spp. on cereals *Cercospora arachidicola* on peanuts and other *Cercospora* species on for example sugar beet, bananas and soya beans

*Botrytis cinerea* (grey mould) on tomatoes, strawberries, vines and other hosts

*Phytophthora infestans* (late blight) on tomatoes

*Venturia inaequalis* (scab) on apples

Some of the compounds have also shown a broad range of activities against fungi in vitro. They have activity against various post-harvest diseases on fruit (eg. *Penicillium digatatum* and italicum on oranges and *Gloeosporium musarum* on bananas). Further some of the compounds are active as seed dressings against: Fusarium spp., Septoria spp., Tilletia spp. (ie. bunt, a seed borne disease of wheat), Ustilago spp., Helminthosporium spp. on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

The compounds are also useful for the treatment of candidiasis and human dermatophyte infections.

The compounds, and their derivatives as defined above, also have plant growth regulating activities.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. Compounds which are particularly useful in leaf orientation eg. making the leaves of wheat and barley plants more erect, are the compounds numbered 6, 24, 25, 32, 49 and 62 in Table I above. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and perenne, *Agrostis tenuis, Cynodon dactylon* (Bermuda grass), *Dactylis glomerata,* Festuca spp. (eg. *Festuca rubra*) and Poa spp. (eg. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also stunt weed species present in the grasses; examples of such weed species are sedges (eg. Cyperus spp.) and dicotyledonous weeds (eg. daisy, plantain, knotweed, speedwell, thistle, docks and ragwort). The growth of non-crop vegetation (eg. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturising ornamental, household, garden and nursery plants (eg. poinsettias, chrysanthemums, carnations, tulips and daffodils).

As indicated above, the compounds can also be used to stunt woody species. This property can be used to control hedgerows or to shape or reduce the need for pruning, of fruit trees (eg. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, eg. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (eg. rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, eg. as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, eg. improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (eg. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (ie. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus provides a fungicidal or plant growth regulating composition comprising a compound of general formula (I) as hereinbefore defined, or a salt or metal complex thereof; and, optionally, a carrier or diluent.

The invention also provides a method of combating fungi, which comprises applying to a plant, to seed of a plant, or to the locus of the plant or seed, a compound, or salt or metal complex thereof as hereinbefore defined; or a composition containing the same.

The invention also provides a method of regulating plant growth, which comprises applying to the plant, to seed of a plant or to the locus of a plant or seed, a compound, or a salt or metal complex thereof, as hereinbefore defined, or a composition combining the same.

In the foregoing process the following compounds of Table I are especially useful: compounds Nos. 3, 4, 5, 6, 8, 13, 14, 17, 18, 24, 25, 30, 32, 49, 61, 62, 63, 69, 70 and 72. These compounds have the chemical names;

2-(4-chlorophenyl)-2-(1,2,4-triazol-1-yl)methyl-3-prop-1-yltetrahydrofuran (Compound No. 3);

2-(4-chlorophenyl)-2-(1,2,4-triazol-1-yl)methyl-4-prop-1-yltetrahydrofuran (Compound No. 4);

2-(4-chlorophenyl)-2-(1,2,4-triazol-1-yl)methyl-3-ethyl-tetrahydrofuran (Compound No. 5);
2-(4-chlorophenyl)-2-(1,2,4-triazol-1-yl)methyl-5,5-dimethyltetrahydrofuran (Compound No. 6);
2-(4-chlorophenyl)-2-(1,2,4-triazol-1-yl)methyl-4-ethyl-tetrahydrofuran (Compound No. 8);
2-(4-chlorophenyl)-2-(1,2,4-triazol-1-yl)methyl-4-methyltetrahydrofuran (Compound No. 13);
2-(4-chlorophenyl)-2-(1,2,4-triazol-1-yl)methyl-3-methyltetrahydrofuran (Compound No. 14);
2-(2,4-dichlorophenyl)-2-(1,2,4-triazol-1-yl)methyl-4-prop-1-yltetrahydrofuran (Compound No. 17);
2-(2,4-dichlorophenyl)-2-(1,2,4-triazol-1-ylmethyltetrahydrofuran (Compound No. 18);
2-(4-chlorophenyl)-2-(1,2,4-triazol-1-yl)methyl-5-methyltetrahydrofuran, diastereomer A (Compound No. 24);
2-(4-chlorophenyl)-2-(1,2,4-triazol-1-yl)methyl-5-methyltetrahydrofuran, diastereomer B (Compound No. 25);
2-(4-chlorophenyl)-2-(1,2,4-triazol-1-yl)methyl-5-methyl-5-prop-1-yltetrahydrofuran, diastereomer B (Compound No. 30);
2-(4-chlorophenyl)-2-(1,2,4-triazol-1-yl)methyl-5-methyl-5-but-1-yltetrahydrofuran, diastereomer B, (Compound No. 32);
2-(2-chlorophenyl)-2-(1,2,4-triazol-1-yl)methyl-5-methyltetrahydrofuran, diastereomer A, (Compound No. 49).
2-(2,4-dichlorophenyl)-2-(1,2,4-triazol-1-yl)methyl-5-methyltetrahydrofuran (Compound No. 61);
2-(4-chlorophenyl)-2-(1,2,4-triazol-1-yl)methyl-4,4-dimethyltetrahydrofuran (Compound No. 62);
2-(2,4-dichlorophenyl)-2-(1,2,4-triazol-1-yl)methyl-5,5-dimethyltetrahydrofuran (Compound No. 63);
2-(4-isopropylphenyl)-2-(1,2,4-triazol-1-yl)methyl-5,5-dimethyltetrahydrofuran (Compound No. 69);
2-(4-methylphenyl)-2-(1,2,4-triazol-1-yl)methyl-5,5-dimethyltetrahydrofuran (Compound No. 70); and
2-(4-methoxyphenyl)-2-(1,2,4-triazol-1-yl)methyl-5,5-dimethyltetrahydrofuran (Compound No. 72);

The compounds, salts, metal complexes, ethers and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dipersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (eg. 2-ethoxyethanol and 2-butoxyethanol).

The compositions to be used as sprays may also be in the form of aerosols wherein the formulation is held in a container under pressure in the presence of a propellant, eg. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants eg. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10-85%, for example 25-60%, by weight of the active ingredient(s). These concentrates suitably contain organic acids (eg. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also other compound(s) having biological activity, eg. compounds having similar or complementary fungicidal or plant growth activity or compounds having plant growth regulating, herbicidal or insecticidal activity.

The other fungicidal compound can be, for example, one which is capable of combating ear diseases of cereals (eg. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenaponil, ofurace, propiconazole, etaconazole and fenpropemorph.

The compounds of general formula (I) can be mixed with soil, peat or other rooting media for the protection of plants against seed-borne, soil-borne or foliar fungal diseases.

Suitable insecticides are Pirimor, Croneton, dimethoate, Metasystox and formothion.

The other plant growth regulating compound can be one which controls weeds or seedhead formation, improves the level or longevity of the plant growth regulating activity of the compounds of general formula (I), selectively controls the growth of the less desirable plants (eg. grasses) or causes the compound of general formula (I) to act faster or slower as a plant growth regulating agent. Some of these other agents will be herbicides.

Examples of suitable plant growth regulating compounds, which can display synergy in admixture, or use, with the invention compounds are the gibberellins (eg. $GA_3$, $GA_4$ or $GA_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acids (eg. triiodobenzoic acid), morphactins (eg. chlorfluorecol), maleic hydrazide, glyphosate, glyphosine, long chain fatty alcohols and acids, dikegulac, fluoridamid, mefluidide, substituted quaternary ammonium and phosphonium compounds (eg. chlormequat* chlorphonium or mepiquat chloride*), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat*, benzoylprop-ethyl 3,6-dichloropicolinic acid, and tecnazene. Synergy will be most likely to occur with those of the foregoing which are quaternary ammonium compounds and with those marked with an asterisk.

The use of the compounds of general formula (I) in conjunction with gibberellins can be useful where it is desired to reduce the plant growth regulating effects of the compounds (eg. where they are to be used as fungicides). Where the compounds are being applied to the soil surrounding the plants or to the roots of the plant, the plant growth regulating effects of the compounds may possibly be reduced by using also certain types of phenoxybenzoic acids and their derivatives.

The following Examples illustrate the invention; the temperatures are given in degrees Centrigrade (°C.).

EXAMPLE 1

This Example illustrates the preparation of 2-(4-chlorophenyl)-2-(1,2,4-triazol-1-yl)methyl-5-prop-1-yltetrahydrofuran (compound numbers 15 and 16 of Table I).

A solution of 4-chlorobenzaldehyde (23.4 g) in dry dimethylformamide (DMF: 100 ml) was added over 10 minutes to a stirred mixture of sodium cyanide (4.0 g) and dry DMF (200 ml). After 5 minutes a solution of methyl acrylate (10.75 g) in dry DMF (100 ml) was added to the reaction mixture over 20 minutes. The temperature of the reaction mixture was maintained at 35° C. throughout both additions and then for a further 3 hours before it was poured into water and extracted with diethyl ether. The extracts were washed successively with water (several times), dilute sulphuric acid, aqueous sodium bicarbonate, and water, before drying over magnesium sulphate and concentration under reduced pressure to give methyl 3-(4-chlorobenzoyl)-propanoate (24.4 g, 86%) as a yellow solid.

A suspension of sodium hydride (1.8 g) in dry dimethylsulphoxide (DMSO: 50 ml) was stirred at 60° under an atmosphere of nitrogen for 2.5 hours. The resulting clear solution was cooled in an ice-water bath, a solution of methyltriphenylphosphonium bromide (26.8 g) in dry DMSO (100 ml) was added, and the resulting dark yellow ylide solution was allowed to warm to room temperature over 10 minutes. A solution of methyl 3-(4-chlorobenzoyl)propanoate (11.4 g) in dry DMSO (50 ml) was added and the reaction mixture was stirred at room temperature for 2.5 hours. It was poured into water and extracted with diethyl ether. The extracts were washed with water, dried over magnesium sulphate, and concentrated under reduced pressure to give a red oily solid (20 g). Chromatography on a column of silica gel using dichloromethane as eluent gave methyl 4-(4-chlorophenyl)pent-4-enoate (6.6 g, 62%) as an orange oil, $^1$H nmr (CDCl$_3$): δ5.1 (1H, broad singlet) and 5.3 (1H, singlet), =CH$_2$.

A solution of methyl 4-(4-chlorophenyl)pent-4-enoate (5.5 g) in dry diethyl ether (20 ml) was added dropwise over 10 minutes to a stirred suspension of lithium aluminium hydride (1.9 g) in dry diethyl ether (130 ml), cooled in an ice-water bath and under an atmosphere of nitrogen. Following the addition, the cooling bath was removed and the reaction mixture was stirred for 1 hour at room temperature and then diluted with aqueous ammonium chloride. The mixture was extracted with diethyl ether, and the extracts were washed with water, dried over magnesium sulfate, and concentrated under reduced pressure to give 4-(4-chlorophenyl)pent-4-en-1-ol (4.5 g, 93%) as a pale yellow oil, IR (film): 3400 cm$^{-1}$.

A mixture of 4-(4-chlorophenyl)pent-4-en-1-ol (5.5 g) and pyridinium dichromate (14.62 g) in dichloromethane (50 ml) was stirred at room temperature for 24 hours. The mixture was diluted with diethyl ether and the solid material was filtered off. The filtrate was washed with water, dried over magnesium sulfate, and concentrated under reduced pressure to give 4-(4-chlorophenyl)pent-4-enal (2.6 g, 48%) as a yellow oil, $^1$H nmr (CDCl$_3$): 9.75 (1H, broad singlet, CHO), IR (film): 1720 cm$^{-1}$.

A solution of 4-(4-chlorophenyl)pent-4-enal (2.0 g) in dry diethyl ether (25 ml) was added to a stirred solution of propylmagnesium iodide [from 1-iodopropane (2.72 g) and magnesium turnings (0.48 g)] in dry diethyl ether (50 ml) under an atmosphere of nitrogen (exotherm). After stirring for 1 hour the reaction mixture was poured into a mixture of ice and dilute sulphuric acid, then extracted with ether. The extracts were washed with water, dried over magnesium sulphate, and concentrated under reduced pressure to give 2-(4-chlorophenyl)-5-hydroxyoct-1-ene (1.9 g, 77%) as a yellow oil.

A solution of bromine (1.28 g) in dichloromethane (25 ml) was added dropwise over 15 minutes to a stirred solution of 2-(4-chlorophenyl)-5-hydroxyoct-1-ene (1.9 g) and pyridine (0.63 g) in dichloromethane (25 ml) at 0° to 5° C. (decolourisation of bromine and mild exotherm). The cooling bath was removed and the mixture was stirred for a further 30 minutes, then washed successively with water, dilute hydrochloric acid, aqueous sodium bicarbonate, and water, then dried over magnesium sulphate and concentrated under reduced pressure to give 2-(4-chlorophenyl)-2-bromomethyl-5-prop-1-yltetrahydrofuran (2.6 g) as a red oil, $^1$H nmr (CDCl$_3$): δ3.9 (2H, singlet, CH$_2$Br).

A solution of 2-(4-chlorophenyl)-2-bromomethyl-5-prop-1-yltetrahydrofuran (2.54 g) in dry DMF (25 ml) was added to a stirred solution of sodium triazole [from 1,2,4-triazole (1.11 g) and sodium hydride (0.38 g)] in dry DMF (25 ml) under an atmosphere of nitrogen, and the mixture was heated at 160° for 4 hours. The reaction mixture was poured into water and extracted with diethyl ether. The extracts were washed with water, dried over magnesium sulphate, and concentrated under reduced pressure to give a red oil (1.5 g). Chromatography on a column of silica gel using diethyl ether as eluent gave the title compound as two distinct diastereoisomers: Isomer A, 185 mg [8% from 2-(4-chlorophenyl)-5-hydroxyoct-1-ene] of a slightly sticky solid, m.p. 55°–61° C., $^1$H nmr (CDCl$_3$): δ3.90 (1H, multiplet, HCO) and two doublets, each J 14 Hz, centred at δ4.33 (CH$_2$N), R$_f$ (diethyl ether on silica gel) 0.3; Isomer B, 390 mg [16% from 2-(4-chlorophenyl)-5-hydroxyoct-1-ene] of a pale yellow solid, m.p. 66°–67° C., $^1$H nmr (CDCl$_3$): 3.85 (1H, multiplet, HCO) and two doublets, each J 14 Hz, centred at δ4.37 (CH$_2$N), R$_f$ (diethyl ether on silica gel) 0.2.

EXAMPLE 2

This Example illustrates the preparation of 2-(4-chlorophenyl)-2-(1,2,4-triazol-1-yl)methyl-5,5-dimethyltetrahydrofuran (compound number 6 of Table I).

A solution of methyl 4-(4-chlorophenyl)pent-4-enoate (5.8 g, prepared as described in Example 1) in dry diethyl ether (25 ml) was added to a stirred solution of methylmagnesium iodide [from methyl iodide (8.52 g) and magnesium turnings (1.7 g)] in dry diethyl ether (50 ml) (exotherm). After 1 hour at room temperature the reaction mixture was poured into a mixture of ice and dilute sulphuric acid, then extracted with diethyl ether. The extracts were washed with water, dried over magnesium sulphate, and concentrated under reduced pressure to give 2-(4-chlorophenyl)-5-hydroxy-5-methylhex-1-ene (5.8 g, quantitative) as a yellow oil, $^1$H nmr (CDCl$_3$): δ1.22 (6H, singlet, CH$_3$×2).

By the cyclisation procedure described for the preparation of 2-(4-chlorophenyl)-2-bromomethyl-5-prop-1-yltetrahydrofuran (see Example 1), 2-(4-chlorophenyl)-5-hydroxy-5-methylhex-1-ene (5.3 g), bromine (3.8 g), and pyridine (1.9 g), in dichloromethane (60 ml), gave 2-(4-chlorophenyl)-2-bromomethyl-5,5-dimethyltetrahydrofuran (7.6 g) as a red oil, $^1$H nmr (CDCl$_3$): δ1.2 (3H, singlet) and 1.4 (3H, singlet), 2×CH$_3$, 3.5 (2H, singlet, CH$_2$Br).

By the displacement procedure described for the preparation of 2-(4-chlorophenyl)-2-(1,2,4-triazol-1-yl)methyl-5-prop-1-yltetrahydrofuran (see Example 1), 2-(4-chlorophenyl)-2-bromomethyl-5,5-dimethyltetrahydrofuran (3.5 g), 1,2,4-triazole (1.24 g) and sodium hydride (0.43 g) in dry dimethylformamide (40 ml) gave the title compound [1.32 g, 39% from methyl 4-(4-chlorophenyl)pent-4-enoate] as a white solid, m.p. 79°–80° C., $^1$H nmr (CDCl$_3$): δ1.13 (3H, singlet) and 1.20 (3H, singlet), 2×CH$_3$; (Found: C,61.94; H,6.16;

N,14.38%. $C_{15}H_{18}ClN_3O$ requires C,61.75; H,6.17; N,14.41%).

EXAMPLE 3

This Example illustrates the preparation of 2-(4-chlorophenyl)-2-(1,2,4-triazol-1-yl)methyl-3-ethyltetrahydrofuran (compound number 5 of Table I).

By the procedure described for the preparation of methyl 3-(4-chlorobenzoyl)propanoate (see Example 1), 4-chlorobenzaldehyde (22.48 g), methyl pent-2-enoate (13.65 g), and sodium cyanide (3.92 g) in dry dimethylformamide (DMF: 250 ml), followed by column chromatography on silica gel using dichloromethane: 40°–60° petrol (1:2) as eluent, gave methyl 3-(4-chlorobenzoyl)pentanoate (6.5 g, 21%) as a yellow oil.

By the procedure described for the preparation of methyl 4-(4-chlorophenyl)pent-4-enoate (see Example 1), except the reaction mixture was stirred for 1 hour at room temperature and 1 hour at 50° C., methyl 3-(4-chlorobenzoyl)pentanoate (5.9 g), methyltriphenylphosphonium bromide (12.5 g), and sodium hydride (0.84 g) in dry dimethylsulphoxide (150 ml) gave methyl 3-ethyl-4-(4-chlorophenyl)pent-4-enoate (2.0 g, 34%) as a yellow oil, $^1$H nmr (CDCl$_3$): δ5.03 (1H, broad singlet) and 5.22 (1H, singlet), =CH$_2$.

By the procedure described for the preparation of 4-(4-chlorophenyl)pent-4-en-1-ol (see Example 1), methyl 3-ethyl-4-(4-chlorophenyl)pent-4-enoate (1.50 g) and lithium aluminium hydride (0.57 g) in dry diethyl ether (50 ml) gave 3-ethyl-4-(4-chlorophenyl)pent-4-en-1-ol (1.40 g, quantitative) as a pale yellow oil.

By the cyclisation procedure described for the preparation of 2-(4-chlorophenyl)-2-bromomethyl-5-prop-1-yltetrahydrofuran (see Example 1), 3-ethyl-4-(4-chlorophenyl)pent-4-en-1-ol (1.20 g), bromine (0.86 g), and pyridine (0.43 g) in dichloromethane gave 2-(4-chlorophenyl)-2-bromo-methyl-3-ethyltetrahydrofuran (1.60 g) as a red oil.

By the displacement procedure described for the preparation of 2-(4-chlorophenyl)-2-(1,2,4-triazol-1-yl)methyl-5-prop-1-yltetrahydrofuran (see Example 1), 2-(4-chlorophenyl)-2-bromomethyl-3-ethyltetrahydrofuran (1.40 g), 1,2,4-triazole (0.62 g), and sodium hydride (0.22 g) in dry DMF (35 ml) gave the title compound (0.35 g, 27% from methyl 3-ethyl-4-(4-chlorophenyl)pent-4-enoate) as a white solid (ca. 19:1 mixture of diastereoisomers), m.p. 100°–105° C., $^1$H nmr (CDCl$_3$): δ4.52 (2H, singlet, CH$_2$N). (Found: C,61.59; H,6.15; N,13.85%. $C_{15}H_{18}ClN_3O$ requires C,61.75; H,6.17; N,14.41%).

EXAMPLE 4

This Example illustrates the preparation of 2-(2,4-dichlorophenyl)-2-(1,2,4-triazol-1-yl)methyl-4-prop-1-yltetrahydrofuran (compound number 17 of Table I).

A solution of 2,4-dichlorobenzaldehyde (21.0 g) in dry tetrahydrofuran (THF: 100 ml) was added slowly to a stirred solution of the Grignard reagent formed from 2-(2-chloroethyl)-1,3-dioxane (18.0 g) and magnesium turnings (3.9 g) in dry THF (100 ml) under an atmosphere of nitrogen at room temperature (exotherm). After 1 hour at room temperature the reaction mixture was poured into a mixture of ice and ammonium chloride which was then extracted with diethyl ether. The extracts were washed with water, dried over magnesium sulphate, and concentrated under reduced pressure to give 2-[3-hydroxy-3-(2,4-dichlorophenyl)-prop-1-yl]-1,3-dioxane (36.5 g, quantitative) as a yellow oil, IR (film): 3420 cm$^{-1}$.

A mixture of 2-[3-hydroxy-3-(2,4-dichlorophenyl)-prop-1-yl]-1,3-dioxane (2.91 g) and pyridinium dichromate (6.96 g) in dry dimethylformamide (DMF: 20 ml) was stirred at room temperature for 7 hours. The reaction mixture was diluted with water (100 ml) and extracted with diethyl ether. The extracts were washed with water, dried over magnesium sulphate, and concentrated under reduced pressure to give 2-[2-(2,4-dichlorobenzoyl)ethyl]-1,3-dioxane (2.7 g, 93%) as an orange oil, IR (film): 1700 cm$^{-1}$.

By the procedure described for the preparation of methyl 4-(4-chlorophenyl)pent-4-enoate (see Example 1), except that the reaction mixture was stirred for 1 hour at room temperature and 1 hour at 50° C., 2-[2-(2,4-dichlorobenzoyl)ethyl]-1,3-dioxane (15.0 g), methyltriphenylphosphonium bromide (25.0 g), and sodium hydride (1.56 g) in dry dimethylsulphoxide (200 ml) gave 2-[3-(2,4-dichlorophenyl)but-3-en-1-yl]-1,3-dioxane (9.3 g, 62%) as a yellow oil, $^1$H nmr (CDCl$_3$): δ5.02 (1H, singlet) and 5.30 (1H, broad singlet), =CH$_2$.

A mixture of 2-[3-(2,4-dichlorophenyl)but-3-en-1-yl]-1,3-dioxane (13.5 g) and oxalic acid (8.0 g) in water (100 ml) was heated in a flask fitted with a steam inlet and an anti-splash still head and condenser. The distillate, collected until almost no immiscible oily globules remained in the reaction flask, was extracted with diethyl ether. The extracts were washed with aqueous sodium bicarbonate and aqueous sodium chloride, the dried over magnesium sulphate and concentrated under reduced pressure to give 4-(2,4-dichlorophenyl)pent-4-enal (9.21 g, 86%), containing a trace of the reactant, as a pale yellow oil, $^1$H nmr (CDCl$_3$): δ9.84 (1H, t J 2 Hz, CHO).

A solution of 4-(2,4-dichlorophenyl)pent-4-enal (10.66 g) and tert-butylamine (4.08 g) in hexane were refluxed under Dean and Stark conditions for 4 hours, and the hexane and excess amine were stripped off under reduced pressure to give the crude imine as a yellow oil whose infrared spectrum showed no carbonyl absorption and a peak at 1670 cm$^{-1}$. A solution of this imine in dry tetrahydrofuran was added to a stirred solution of propylmagnesium iodide [from 1-iodopropane (7.92 g) and magnesium turnings (1.12 g)] in tetrahydrofuran under an atmosphere of nitrogen and the mixture was heated under reflux for 3 hours.

1-Iodopropane (7.92 g) was added and the reaction mixture was heated under reflux for a further 14 hours. An excess of 10% hydrochloric acid was added and the reaction mixture was refluxed for 2 hours, then extracted with diethyl ether. The extracts were washed with aqueous sodium bicarbonate, dried over magnesium sulphate, concentrated under reduced pressure, and chromatographed on a column of silica gel using dichloromethane: 40°–60° petrol (1:1) as eluent to give 4-formyl-2-(2,4-dichlorophenyl)hept-1-ene (1.71 g, 20%) as a yellow oil, $^1$H nmr (CDCl$_3$): δ0.84 (3H, t J 7 Hz, CH$_3$), 9.73 (1H, d J 3 Hz, CHO).

By the procedure described for the preparation of 4-(4-chlorophenyl)pent-4-en-1-ol (see Example 1), 4-formyl-2-(2,4-dichlorophenyl)hept-1-ene (1.7 g) and lithium aluminium hydride (0.5 g) in dry diethyl ether (30 ml) gave 4-(hydroxymethyl)-2-(2,4-dichlorophenyl)hept-1-ene (1.55 g, 91%) as a colourless oil, $^1$H nmr (CDCl$_3$): δ3.52 (2H, d J 6 Hz, CH$_2$OH).

By the cyclisation procedure described for the preparation of 2-(4-chlorophenyl)-2-bromomethyl-5-prop-1-yltetrahydrofuran (see Example 1), 4-(hydroxymethyl)-

2-(2,4-dichlorophenyl)hept-1-ene (1.5 g), bromine (0.88 g), and pyridine (0.43 g) in dry dichloromethane (30 ml) gave 2-(2,4-dichlorophenyl)-2-bromomethyl-4-prop-1-yltetrahydrofuran (1.9 g, 98%) as a pale yellow oil.

By the displacement procedure described for the preparation of 2-(4-chlorophenyl)-2-(1,2,4-triazol-1-yl)methyl-5-prop-1-yltetrahydrofuran (see Example 1), 2-(2,4-dichlorophenyl)-2-bromomethyl-4-prop-1-yltetrahydrofuran (1.8 g), 1,2,4-triazole (1.04 g), and sodium hydride (0.36 g) in dry dimethylformamide (30 ml) gave the title compound (1.12 g, 60%) as a yellow oil (3:1 mixture of diastereoisomers), $^1$H nmr (CDCl$_3$): δ3.39 and 4.07 (each 1H, pseudotriplet, J 8 Hz, CH$_2$O of major diastereoisomer).

EXAMPLE 5

This Example illustrates the preparation of 2-(4-chlorophenyl)-2-(1,2,4-triazol-1-yl)methyl-4,4-dimethyltetrahydrofuran, (Compound No. 62 of Table I).

To 2,2-dimethylsuccinic acid (25 g) was added acetyl chloride (35 ml). The mixture was stirred and heated at reflux for 3 hours, then cooled to room temperature. A small quantity of dry ether was added, and the resulting solution left overnight in the fridge. A solid precipitated, and was washed with a little cold ether, then dried in vacuo. Yield: 14.9 g. This 2,2-dimethylsuccinic anhydride was used without further purification.

Finely powdered aluminium chloride (29.35 g), 2,2-dimethylsuccinic anhydride (13.9 g) and chlorobenzene (45 ml) were mixed, then stirred and heated on a boiling-water bath for 1.5 hours. The resulting mixture was cooled to room temperature and then poured onto a mixture of ice and water containing a little hydrochloric acid. The resulting mixture was extracted with ether. The ethereal layer was shaken with 2N sodium hydroxide and the resulting aqueous layer washed with ether, acidified with concentrated hydrochloric acid and then extracted with ether. The ethereal layer was washed with water and brine, and finally dried over magnesium sulphate. Removal of the solvent in vacuo gave 13.9 g of 3-(4-chlorobenzoyl)-2,2-dimethylpropionic acid. I.R. (Nujol Mull): 1680 cm$^{-1}$ (s), 1590 cm$^{-1}$ (s).

3-(4-Chlorobenzoyl)-2,2-dimethylpropionic acid (13.7 g) was dissolved in ethanol (100 ml) which had been saturated with gaseous hydrogen chloride. The solution as refluxed for eight hours. The solvent was distilled off and replaced by ether. The ethereal solution was washed with saturated sodium bicarbonate solution, then with brine, dried over magnesium sulphate and concentrated in vacuo to yield 14.5 g of ethyl 3-(4-chlorobenzoyl)-2,2-dimethylpropionate as an oil.

I.R. (Film): 1720 cm$^{-1}$ (s), 1685 cm$^{-1}$ (s), 1590 cm$^{-1}$ (s).

$^1$H n.m.r. (CDCl$_3$): δ1.2 (3H,t), 1.3 (6H,s), 3.2 (2H,s), 4.1 (2H,s), 7.2–8.0 (4H, m).

By procedures described in previous Examples the above-named ester was converted to the title compound: a white solid, m.p. 86°–7° C., I.R. (Nujol Mull): 1490 cm$^{-1}$ (m), 3140 cm$^{-1}$ (w). $^1$H n.m.r.

$^1$H n.m.r. (CDCl$_3$): δ0.8 (3H,s), 0.9 (3H,s), 2.2 (2H,dd), 3.5 (2H,dd), 4.3 (2H,dd), 7.3 (4H,s), 7.8 (1H,s), 8.0 (1H,s).

EXAMPLE 6

This Example illustrates the preparation of -(4-chlorophenyl)-γ-(1,2,4-triazol-1-yl)methyl-γ-butyrolactone (A).

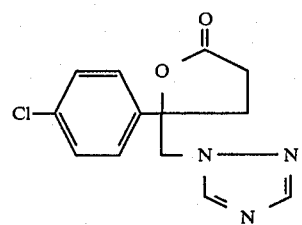

(A)

Ethyl 3-(4-chlorobenzoyl)propanoate (25.0 g, 83%) was prepared from 4-chlorobenzaldehyde (23.4 g), ethyl acrylate (12.5 g) and sodium cyanide (4.0 g) in dimethylformamide (DMF: 300 ml) by the method described for the preparation of the corresponding methyl ester in Example 1.

A suspension of sodium hydride (0.48 g) in dry dimethylsulphoxide (DMSO: 10 ml) was stirred at 50° C. for 2.5 hours. The resulting clear grey solution was allowed to cool, then diluted with tetrahydrofuran (THF: 30 ml) and cooled in an ice-salt bath. Solutions of trimethylsulphonium iodide (4.08 g) in dry DMSO (20 ml) and ethyl 3-(4-chlorobenzoyl)propanoate (4.0 g) in THF (20 ml) were added successively to the reaction mixture at 0° C., and it was allowed to stir for 10 minutes at 0° C. and 1 hour at room temperature before water was added. The mixture was extracted with diethyl ether and the extracts were washed with water, dried over MgSO$_4$, and concentrated to give a red oil (2.54 g) containing ethyl 4-(4-chlorophenyl)-4,5-epoxypentanoate.

A solution of this crude epoxy ester in dry DMF (10 ml) was added to a solution of sodium triazole [from 1,2,4-triazole (1.4 g) and sodium hydride (0.45 g)] in DMF (15 ml) and the resulting mixture was stirred at room temperature for 45 minutes and at 55° C. for 3.5 hours. The mixture was allowed to cool then poured into water and extracted with ether. The extracts were washed with water, dried over MgSO$_4$, and concentrated to give a viscous red oil (1.2 g). Chromatography on a column of silica gel using ethyl acetate as eluant gave a small quantity of the title compound as a viscous yellow oil, R$_f$(EtOAc) 0.2;

IR (film): 1780 cm$^{-1}$; $^1$H n.m.r.

$^1$H n.m.r. (CDCl$_3$): δ2.2–2.8 (4H,m), 4.85 (2H,s), 7.34 (4H, tight AB quartet, almost a singlet), 7.90 (1H,s), 8.10 (1H,s); m/e 279 and 277 (M$^+$ 0.9% and 1.1% respectively); 197 and 195 (M—CH$_2$.C$_2$H$_2$N$_3$, 33.9% and 100% respectively).

EXAMPLE 7

This Example illustrates the preparation of 2-(4-chlorophenyl)-2-[1-(1,2,4-triazol-1-yl)ethyl]-5,5-dimethyltetrahydrofuran (Compound No. 60 of Table I).

A suspension of sodium hydride (1.44 g) in dry dimethylsulphoxide (DMSO: 50 ml) was stirred at 60° C. for 2.5 hours under an atmosphere of nitrogen. The resulting clear solution as cooled in an ice-water bath and a solution of ethyltriphenylphosphonium bromide (23.0 g) in dry DMSO (50 ml) was added; the resulting bright orange-red ylide solution was allowed to warm to room temperature over 10 minutes. A solution of methyl 3-(4-chlorobenzoyl)-propanoate (9.0 g: prepared as described in Example 1) in dry DMSO (50 ml) was added and the reaction mixture was heated at between 60° and 70° C. for 2 hours. The mixture was allowed to cool, poured into water, and extracted with diethyl ether. The extracts were washed with water, dried over magnesium sulphate, and concentrated to give a dark red oil (12.5 g). Chromatography on a column of silica gel using dichloromethane: 40°-60° C. petrol (1:1) as eluant gave methyl 4-(4-chlorophenyl)hex-4-enoate (3.65 g, 38%), a 3:2 mixture of geometric isomers, as an orange oil.

$^1$H n.m.r. (CDCl$_3$): δ1.53 and 1.81 (each d, J 7 Hz, CHCH$_3$), 5.48-5.86 (m,: CHCH$_3$)

IR (film): 1740 cm$^-$.

A solution of methyl 4-(4-chlorophenyl)hex-4-enoate (3.50 g) in dry diethyl ether (20 ml) was added dropwise to a stirred solution of methylmagnesium iodide [from methyl iodide (4.8 g) and magnesium (0.9 g)] in dry diethyl ether (30 ml) under an atmosphere of nitrogen. The reaction mixture was stirred for 1 hour at room temperature, poured into a mixture of ice and dilute sulphuric acid, then extracted with diethyl ether. The extracts were washed with water, dried over magnesium sulphate, and concentrated to give 2-methyl-5-(4-chlorophenyl)hept-5-en-2-ol (3.3 g, 95%), a 3:2 mixture of geometric isomers, as an orange oil.

IR (film): 3400 cm$^{-1}$.

By the method described in Example 1 for the preparation of 2-(4-chlorophenyl)-2-bromomethyl-5-prop-1-yltetrahydrofuran, 2-methyl-5-(4-chlorophenyl)hept-5-en-2-ol (3.2 g), bromine (2.35 g), and pyridine (1.18 g) in dry dichloromethane (40 ml) gave 2-(4-chlorophenyl)-2-(1-bromoethyl)-5,5-dimethyltetrahydrofuran (4.4 g, 94%), a mixture of diastereomers, as an orange oil.

$^1$H n.m.r. (CDCl$_3$): δ4.06-4.40 (1H,m, CH$_3$.CHBr).

A solution of part of the crude bromide (2.0 g) in dry dimethylformamide (DMF: 10 ml) was added to a stirred solution of sodium triazole [from 1,2,4-triazole (0.69 g) and sodium hydride (0.24 g)] in dry DMF (20 ml) under an atmosphere of nitrogen. The mixture was heated under reflux for 7 hours, then poured into water and extracted with ether. The extracts were washed with water, dried over magnesium sulphate, and concentrated to give a yellow oil (1.33 g). Analysis of the crude product by proton n.m.r. spectroscopy showed that it consisted largely of 2-(4-chlorophenyl)-2-vinyl-5,5-dimethyltetrahydrofuran. However, chromatography on a column of silica gel using diethyl ether as eluant enabled a small quantity of the title compound, a 3:1 mixture of diastereomers, as a colourless oil, to be isolated.

$^1$H n.m.r. (CDCl$_3$: δ1.11-1.18 (6H, 3 singlets, THF-ring methyl groups), 1.31-1.178 (5H,m, CH$_3$CHN and two THF-ring protons), 2.11-2.84 (2H,m,THF-ring protons), 4.45-4.79 (1H, 2 overlapping quartets, J 7 Hz, CH$_3$ CHN), 7.41 and 7.48 (4H,2 singlets, phenyl ring protons), 8.04, 8.09, 8.19 and 8.32 (2H, 4 singlets, triazole protons). MS (electron ionisation): 308 and 306 (1.2% and 2.6% respectively, MH+), 211 and 209 (28.6% and 83.5% respectively, M-CH$_3$CH.C$_2$H$_2$N$_3$), 141 and 139 (33.9% and 100% respectively, CO.C$_6$H$_4$Cl); (chemical ionisation: isobutane): 308 and 306 (35% and 100% respectively, MH+).

EXAMPLE 8

An emulsifiable concentrate was made up by mixing the ingredients, and stirring the mixture until all the constituents were dissolved.

| | |
|---|---|
| Compound of Example 2 | 10% |
| Ethylene dichloride | 40% |
| Calcium dodecylbenzenesulphate | 5% |
| "Lubrol" L | 10% |
| "Aromasol" H | 35% |

EXAMPLE 9

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44-100, to obtain the desired size of grains.

| | |
|---|---|
| Compound of Example 2 | 50% |
| "Dispersol" T | 25% |
| "Lubrol" APN5 | 1.5% |
| Sodium acetate | 23.5% |

EXAMPLE 10

The ingredients were all ground together to produce a powder formulation readily dispersible in liquids.

| | |
|---|---|
| Compound of Example 2 | 45% |
| "Dispersol" T | 5% |
| "Lissapol" NX | 0.5% |
| "Cellofas" B600 | 2% |
| Sodium acetate | 47.5% |

EXAMPLE 11

The active ingredient was dissolved in a solvent and the resultant liquid was sprayed on to the granules of China clay. The solvent was then allowed to evaporate to produce a granular composition.

| | |
|---|---|
| Compound of Example 2 | 5% |
| China clay granules | 95% |

EXAMPLE 12

A composition suitable for use as a seed dressing was prepared by mixing the three ingredients.

| | |
|---|---|
| Compound of Example 2 | 50% |
| Mineral oil | 2% |
| China clay | 48% |

EXAMPLE 13

A dusting powder was prepared by mixing the active ingredient with talc.

| | |
|---|---|
| Compound of Example 2 | 5% |
| Talc | 95% |

EXAMPLE 14

A Col formulation was prepared by ball-milling the constituents set out below and then forming an aqueous suspension of the ground mixture with water.

| | |
|---|---|
| Compound of Example 2 | 40% |
| "Dispersol" T | 10% |
| "Lubrol" APN5 | 1% |
| Water | |

EXAMPLE 15

A dispersible powder formulation was made by mixing together the ingredients set out below and then grinding the mixture until all were thoroughly mixed.

| | |
|---|---|
| Compound of Example 2 | 25% |
| "Aerosol" OT/B | 2% |
| "Dispersol" A.C. | 5% |
| China clay | 28% |
| Silica | 40% |

EXAMPLE 16

This Example illustrates the preparation of a dispersible powder formulation. The ingredients were mixed and the mixture then ground in a comminution mill.

| | |
|---|---|
| Compound of Example 2 | 25% |
| "Perminal" BX | 1% |
| "Dispersol" T | 5% |
| Polyvinylpyrrolidone | 10% |
| Silica | 25% |
| China clay | 34% |

EXAMPLE 17

The ingredients set out below were formulated into a dispersible powder by mixing then grinding the ingredients.

| | |
|---|---|
| Compound of Example 2 | 25% |
| "Aerosol" OT/B | 2% |
| "Dispersol" A | 5% |
| China clay | 68% |

In Examples 9 to 17 the proportions of the ingredients given are by weight.

The remaining compounds of Table No. 1 above were similarly formulated.

There now follows an explanation of the compositions or substances represented by the various Trade Marks and Trade Names mentioned above.

| | |
|---|---|
| LUBROL L: | a condensate of nonyl phenol (1 mole) with ethylene oxide (13 moles) |
| AROMASOL H: | a solvent mixture of alkylbenzenes |
| DISPERSOL T & AC: | a mixture of sodium sulphate and a condensate of formaldehyde with sodium naphthalene sulphonate |
| LUBROL APN5: | a condensate of nonyl phenol (1 mole) with naphthalene oxide (5.5 moles) |
| CELLOFAS B600: | a sodium carboxymethyl cellulose thickener |
| LISSAPOL NX: | a condensate of nonyl phenol (1 mole) with ethylene oxide (8 moles) |
| AEROSOL OT/B: | dioctyl sodium sulphosuccinate |
| PERMINAL BX: | a sodium alkyl naphthalene sulphonate |

EXAMPLE 18

The compounds were tested against a variety of mainly foliar fungal diseases of plants. The techniques employed were as follows.

For all tests other than that against *Botrytis cinerea*, the plants were grown in John Innes Potting Compost (No. 1 or 2) in 4 cm diameter minipots. A layer of fine sand was placed at the bottom of the pots containing the dicotyledonous plants to facilitate uptake of test compounds by the roots. The test compounds were formulated either by bead milling with aqueous Dispersol T or as a solution in acetone or acetone/ethanol which was diluted to the required concentration immediately before use. For the foliage diseases, solutions and suspensions (100 ppm ai.) were sprayed on the foliage and applied to the roots of the plant via the soil. For the test against *Botrytis cinerea*, grape berries were sprayed with the test compounds. The sprays were applied to maximum retention and the root drenches to a final concentration equivalent to approximately 40 ppm ai./dry soil. Tween 20, to give a final concentration of 0.05%, was added when the sprays were applied to cereals. (ai. means "active ingredient").

Most were protectant tests where the compound was applied to the soil and roots and to the foliage one or two days before the plant was inoculated with the pathogen. However, in the case of the tests against *Erisyphe graminis* hordei and *Botrytis cinerea*, the treatment was eradicative and the compounds were applied one day after inoculation.

Inoculation of the grape berries in the *Botrytis cinerea* test was achieved by slitting fruits twice and then immersing them in a spore suspension of the pathogen. The remaining foliar pathogens were applied by spraying as spore suspensions onto the leaves of the test plants.

After inoculation, the plants were placed in an appropriate environment to allow infection to proceed and then incubated until the disease was ready for assessment. The period between inoculation and assessment varied from four to fourteen days according to the disease and the environment.

Disease control was recorded using the following grading system:

4 = no disease
3 = trace to 5% of disease on untreated plants
2 = 6–25% of disease on untreated plants
1 = 26–59% of disease on untreated plants
0 = 60–100% of disease on untreated plants The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (GRAPE) | CERCOSPORA ARACHIDICOLA (PEANUT) | VENTURIA INAEQUALIS (APPLE) |
|---|---|---|---|---|---|---|---|---|
| 1 | 4 | 4 | — | 0 | — | — | 4 | 4 |
| 2 | 0 | 4 | — | 0 | — | — | 2 | 3 |

TABLE II-continued

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (GRAPE) | CERCOSPORA ARACHIDICOLA (PEANUT) | VENTURIA INAEQUALIS (APPLE) |
|---|---|---|---|---|---|---|---|---|
| 3 | 4 | 4 | — | 1 | — | 0 | 4 | 4 |
| 4A | 4 | 4 | — | 0 | — | 0 | 2 | 4 |
| 4B | 4 | 4 | — | 1 | — | 0 | 4 | 4 |
| 4C | — | — | — | — | — | — | — | — |
| 5A | 4 | 4 | — | 1 | — | 0 | 4 | 4 |
| 5B | — | — | — | — | — | — | — | — |
| 6 | 4 | 4 | — | 1 | — | 0 | 4 | 4 |
| 7 | 4 | 4 | — | 0 | — | 0 | 1 | 0 |
| 8 | 4 | 4 | — | 1 | — | 4 | 4 | 4 |
| 9 | 4 | 4 | — | 2 | — | 0 | 3 | 4 |
| 10 | 4 | 4 | — | 0 | — | 0 | 3 | 4 |
| 11 | 3 | 4 | — | 2 | — | 0 | 3 | 3 |
| 12 | 1 | 4 | — | 0 | — | 0 | 1 | 4 |
| 13 | 4 | 4 | — | 0 | — | 0 | 4 | 4 |
| 14 | 4 | 4 | — | 0 | — | 0 | 4 | 4 |
| 15 | 4 | 4 | — | 0 | — | 0 | 3 | 4 |
| 16 | 4 | 4 | — | 0 | — | 0 | 3 | 2 |
| 17 | 4 | 4 | — | 0 | — | 0 | 4 | 4 |
| 18 | 4 | 4 | — | 0 | — | 0 | 4 | 4 |
| 19 | 4 | 4 | 3 | 3 | — | 0 | 4 | 4 |
| 20 | 4 | 4 | 2 | 2 | — | 0 | 3 | 3 |
| 21 | 4 | 4 | 2 | 0 | — | — | 4 | 4 |
| 22 | 0 | 4 | 2 | 0 | — | 0 | 4 | 2 |
| 23 | 0 | 4 | 0 | 2 | — | 0 | 1 | 0 |
| 28 | 2 | 4 | 3 | 0 | — | 0 | 3 | 2 |
| 31 | 0 | 4 | 2 | 0 | — | — | 0 | 0 |
| 32 | 0 | 4 | 2 | 0 | — | — | 3 | 0 |
| 41B | 4 | 4 | 3 | 0 | — | — | — | 4 |
| 48 | 4 | 4 | 3 | 3 | — | — | 4 | 2 |

"—" means not tested.
A, B or C placed after a compound number means that in this instance the test results are for different diastereosomeric mixtures of the compound.

EXAMPLE 19

This Example illustrates the plant growth regulating properties of the compounds. The compounds were applied as an overall spray of an emulsifiable concentrate diluted to give the concentrations shown in Table III. The plants were grown in 3" pots in peat compost and sprayed at the 2 leaf stage. Plant growth regulating effects were assessed 13 or 19 days after application of the compounds. Retardation of growth was scored on a 1-3 scale where:

1 = 0-30% retardation
2 = 31-75% retardation
3 = 75% retardation or more.
The absence of any numeral 1 to 3 signifies no effect.
Additional plant growth regulating properties are indicated as follows:
G = darker green leaf colour
A = apical effect
T = tillering effect
The results are shown in Table III. If no figure is shown the compound was substantially inactive as a stunting agent.

TABLE III

| COMPOUND | DAT | RATE (ppm) | AT | CC | DA | LT | SB | TO | SY | CT | MZ | WW | BR |
|---|---|---|---|---|---|---|---|---|---|---|---|---|---|
| 1 | 13 | 4000 | 2 | 1 | | | 2G | 2 | 2GAT | AT | 3G | | T |
| 2 | 13 | 4000 | | | | 1 | G | | 1G | | 1 | | T |
| 3 | 12 | 4000 | 2 | 3 | 2 | 3GA | 3GA | 3GA | 3G | 2A | 2 | 1T | |
| 4A | 12 | 4000 | 2G | 2G | | 3GA | 2A | 3GA | 2GA | | | 1 | 1 |
| 4B | 19 | 4000 | 2G | 2 | 1 | | 3G | | 2GT | 1 | 3 | 1 | 2 |
| 5A | 19 | 4000 | 3G | 2G | 1G | 3G | 3G | 3G | 2G | 3G | 3GA | 2GT | 2GT |
| 6 | 19 | 4000 | 3 | 3 | 3 | 3GA | | 3T | 3GAT | 3A | 3G | 3GT | 2 |
| 8 | 19 | 4000 | 3 | 3 | 2 | 3 | 3GA | 3GA | 3GAT | 2G | 2 | | |
| 10 | 19 | 4000 | | | | 1 | 3GT | 2T | 2T | 2 | | | |
| 12 | 19 | 4000 | 1 | | | 3 | 3G | 3 | 3 | A | | | |
| 13 | 19 | 4000 | 3G | 3G | 3 | 3 | 3G | 3G | 3 | | 3 | 3G | |
| 14 | 19 | 4000 | 3G | 3G | 3G | 3 | 3G | 3G | 3T | | 3G | 3G | 3G |
| 17 | 19 | 4000 | 2G | G | 1G | 3GA | 3GA | 3GA | 3G | 3A | 3 | | |
| 18 | 19 | 4000 | 3 | G | 3GT | 3GA | 3GA | 3GA | 3G | 3A | 3 | 3 | |
| 19 | 12 | 4000 | 1 | 1 | | 1 | 2GA | 2GT | 1GA | 1G | 2G | 1T | 1T |
| 20 | 12 | 4000 | | | | 1 | 3GA | 1GA | 1 | 1 | | | |
| 21 | 12 | 4000 | G | G | G | 2G | 3G | 2GT | 2G | G | 2 | 1T | 1 |
| 22 | 12 | 4000 | 2 | 1 | 1 | 2 | 3G | 2G | 2GA | 2GA | 1 | T | 1T |
| 23 | 12 | 4000 | 1 | | 2 | 3 | 3GA | 2GAT | 2G | 2GA | 3 | T | 1T |
| 24 | 12 | 4000 | 2G | 2G | 2G | 3G | 3G | 2GA | 2GT | 1GAT | 2G | 2GT | 2GT |
| 25 | 12 | 4000 | 2G | 2G | 1G | 2G | 3G | 2GT | 2GAT | 1GAT | 2G | 2GT | 2GT |
| 26 | 12 | 4000 | 1 | 1 | 1 | 2G | 3G | 3GAT | 1G | 1GA | 1G | 1GT | 1GT |
| 27 | 12 | 4000 | 1G | 1G | 1 | 1 | 3G | 2GAT | 1G | 2GA | 1G | T | |
| 28 | 12 | 4000 | 2G | 1G | 1 | 1G | 3G | 3GA | 2G | 1GA | 2 | 1 | 1T |
| 29 | 12 | 4000 | 1 | 1 | 1 | 3GA | 3G | 3GAT | 2G | 3GA | 2G | | |
| 30 | 12 | 4000 | 2G | 2G | 1G | 3G | 3G | 3GT | 2G | 2GA | 1G | 1T | 1 |

TABLE III-continued

| COMPOUND | DAT | RATE (ppm) | AT | CC | DA | LT | SB | TO | SY | CT | MZ | WW | BR |
|---|---|---|---|---|---|---|---|---|---|---|---|---|---|
| 31 | 12 | 4000 | 1 | 1 | 1 | 3G | 3G | 3GAT | 2G | 3GA | 1 | 1 | 1 |
| 32 | 12 | 4000 | 1G | 2G | 1G | 1G | 2G | 2GT | 1G | 2G | 1 | 1T | 1 |
| 33 | 12 | 4000 | 1 | 1 | 1 | 2G | 2G | 2GT | 1G | 2G | 1 | 1 | 1 |
| 34 | 12 | 4000 |  |  |  | 2G | 2G | 2G | 1G | 1G |  | 1T | 1T |
| 35 | 12 | 4000 | 2G | 1G |  | 3 | 2G | 2GAT | 1G | 3GA | 1 | 1GT | 1GT |
| 36 | 12 | 4000 |  |  |  | 2G | 3G | 2GT | 2GT | 3G | 2G | 1G | 1G |
| 37 | 12 | 4000 |  |  |  |  | 2G | 1GA | 2G | 3G | 2G |  |  |
| 38 | 12 | 3000 |  |  |  |  | 2G | 2GT | 2G | 3G |  |  |  |
| 39A | 12 | 4000 |  |  |  | 2G | 2G | 1GAT | 1G | 3G | 1 |  |  |
| 40 | 12 | 4000 | 1G | 1G | 1G | 2 | 2G | 1A | 1G | 3G | 2 |  |  |
| 41A | 12 | 4000 | 3G |  |  | 3G | 3G | 2GAT | 2G | 3G | 2G |  |  |
| 41B | 12 | 4000 | 3G | 1G | 1G | 3G | 3G | 3GAT | 2G | 2G | 1 |  |  |
| 42A | 12 | 4000 | 1 | 1 | 1 | 3G | 3G | 2G | 1 | 2G | 1 |  |  |
| 42B | 12 | 4000 | 1 | 1 | 1 | 3G | 3G | 2GAT | 1 | 3G |  |  |  |
| 43 | 18 | 4000 |  | 1 |  | 2G | 1GA |  | 2GAT | 2GAT | 2 | 1 | 1GA |
| 44 | 18 | 4000 | 1G | G | 1G | 2GA | 2GA |  | 2GAT | 3GAT | 2 |  | 1G |
| 45 | 18 | 4000 | 1G | 1G | 1G | 2 | 1G | 1GT | 2GAT | 3AT | 1A |  |  |
| 46 | 18 | 4000 | 2 | 3 | 1G | 2 | 2G | 2GAT | 2GAT | 2GA | 3 |  |  |
| 47 | 18 | 4000 |  |  | 1 | 2G | 2G | 1GT | 2GAT | 2GA | 1 |  |  |
| 48 | 18 | 4000 | 1G | 1G | 1G | 2G | 1 |  | 1G | 2GA |  | 1 | 1 |
| 49 | 18 | 4000 | 1 | 2 | 1 | 1G | 1G | 1G | 2GA | 2A |  |  |  |
| 50 | 18 | 4000 | 2 | 2 | 1 | 2 | 3GA | 2 | 2GAT | 2A |  |  |  |
| 51 | 18 | 4000 | 2 | 2 | 1 | 1 | 2GA | 2GAT | 2GA | 2G | 1 | 1G |  |
| 52A | 18 | 4000 | 1 | 1 | 1 | 2 | 2GA | 3A | 2G | 1 | 3A |  | 1 |
| 52B | 18 | 4000 | 2 | 2 | 1 | 2A | 2G | 2GA | 2GA | 3GA | 2 |  |  |
| 53 | 18 | 4000 | 1 | 1 |  | 1 | 2GA | 3GA | 2GA | 3A | 2 | 1 |  |
| 54 | 18 | 4000 | 1 | 1 |  | 3 | 2G | 2A | 2GA | 2A | 1 |  |  |
| 55 | 18 | 4000 | G |  | 1G | 2GA | 3GA | 3GA | 2G | 3G | 1 | 1 |  |
| 56 | 18 | 4000 | 1G | 1G | 1G | 3GA | 3GA | 3GA | 3GA | 3GA |  |  |  |
| 57 | 18 | 4000 |  |  | 1 | 2GA | 3GA | 3GA | 3GA | 3GA | 1 |  |  |
| 58 | 18 | 4000 | 3 | 3G | 2G | 3GA | 3GA | 3GA | 3GA | 3GA | 1G | 2G | 2G |
| 59 | 18 | 4000 | 1 | 1G | 2G | 2GA | 3GA | 3GAT | 3GAT | 2GA |  | 1G | 1 |
| 61 | 18 | 4000 | 2 | 2 | 2 | 3 | 3GA | 3G | 3GA | 3GAT | 3 | 2 | 2 |
| 62 | 18 | 4000 |  | 2 | 2 | 2 | 3GA | 3GA | 3GA | 2G | 2 | 3GT | 2GT |
| 69 | 18 | 4000 | 2 | 2 | 1 | 2G | 2G | 3GT | 3GAT | 3A | 2 | 1 | 1 |

Key to test species in Table III

| | |
|---|---|
| AT | *Agrostis tenuis* |
| CC | *Cynosurus cristatus* |
| DA | *Dactylis glomerata* |
| LT | *Lactuca sativa* |
| SB | *Beta vulgaris* |
| TO | *Lycopersicum esculentum* |
| SY | *Glycine max* |
| CT | *Gossypium hirsutum* |
| MZ | *Zea mays* |
| WW | *Triticum aestivum* |
| BR | *Hordeum vulgare* |

EXAMPLE 20

This Example demonstrates the plant growth regulating properties of Compound 6 in barley. Compound 6 was formulated as an aqueous emulsifiable concentrate comprising 95% water and 5% of a mixture of cyclohexanone 95%, 'Synperonic' NPE 1800 3.3%, and 'Tween' 85 1.7%, and applied to barley plants at a field equivalent rate of 4 kg ha$^{-1}$ (at a volume equivalent of 1000 liters/hectare). The plants were grown in 4" pots in John Innes No 1 Potting compost, 3 plants per pot, and ten replicate pots were treated when the plants were at the 1 to 1.5 leaf stage (13 days after sowing).

At 14 DAT plant growth regulating effects were scored against untreated plants on a 1-3 scale where:
1 = 1-30% effect
2 = 31-75% effect
3 > 75% effect The absence of any numeral 1 to 3 signifies no effect. Phytotoxicity was scored on a scale of 0-5.

| REP | SCORE | PHYTO | |
|---|---|---|---|
| 1 | Y2D2L1 | 2 | where: Y = decreased overall plant size |
| 2 | Y2D2B1G1L1 | 2 | |
| 3 | Y2D2B1L1 | 2 | |
| 4 | Y1D1 | 1 | D = decreased leaf size or area |
| 5 | Y1D1L2 | 2 | |
| 6 | Y1D1L1 | 2 | L = shorter internodes |
| 7 | Y1D1B1L2G1 | 2 | |
| 8 | Y2D2L2 | 2 | B = decreased leaf number |
| 9 | Y2D2B1L2 | 3 | |
| 10 | Y2D2B1L1 | 2 | G = darker green |

All plants treated with Compound 6 were noted to have strong upright stems and erect leaves. Plants not treated fell over when unsupported. At 36 DAT the plants were assessed for height to the top leaf ligule from soil level.

Mean Height (mm)

Compound 6 69.9
Untreated control 132.4
This represents a 47% reduction in height.

At 84 DAT 3 pots of treated and 3 pots of untreated were sampled and measurements were made of height to topleaf ligule, leaf area fresh wt, dry weight, spikelet number. The results are shown below for mean data.

TABLE IV

| Measurement Made | Compound 6 | UNT Control | % Change from control |
|---|---|---|---|
| Height to top leaf ligule (mm) | 383.8 | 596.2 | −36% |
| Leaf area (cm$^2$) | 331.3 | 400.3 | −17% |
| Fresh wt (g) | 16.57 | 21.56 | −23% |
| Dry wt (g) | 2.95 | 4.16 | −29% |

TABLE IV-continued

| Measurement Made | Compound 6 | UNT Control | % Change from control |
|---|---|---|---|
| Spikelet number on main stem | 48.8 | 49.0 | 0% |

The compound, therefore, retards growth without any adverse effects on reproductive growth.

EXAMPLE 21

This Example illustrates the synergism displayed by a mixture of compound No. 6 of Table I and the substance having the internationally approved common name chlormequat chloride (CCC).

Spring wheat (cv. Timmo) and spring barley (cv. Sundance) were grown in John Innes No. 1 compost in 10 cm diameter pots, there being 4 plants per pot. At the 2-3 leaf stage, mixtures of the test compound (compound No. 6 of Table I) and CCC ("AROTEX" 5C) were applied at a number of rates in a number of combinations. A full treatment list is given below. The word "AROTEX" is a Trade Mark for a commercial preparation containing chlormequat chloride.

Treatment List

| Treatment No. | Rate g/ha (grams per hectare) of Compound No. 6 of Table I | Rate g/ha (grams per hectare) of chlormequat chloride |
|---|---|---|
| 1 | 0 (formulation blank) | 0 (wetter blank) |
| 2 | 0 (formulation blank) | 1000 |
| 3 | 0 (formulation blank) | 4000 |
| 4 | 50 | 0 |
| 5 | 50 | 1000 |
| 6 | 50 | 4000 |
| 7 | 100 | 0 |
| 8 | 100 | 1000 |
| 9 | 100 | 4000 |
| 10 | 500 | 0 |
| 11 | 500 | 1000 |
| 12 | 500 | 4000 |
| 13 | 1000 | 0 |
| 14 | 1000 | 1000 |
| 15 | 1000 | 4000 |
| 16 | Untreated | |

Compound No 6 was formulated as an emulsifiable concentrate comprising 95% by weight of water and 5% of a formulation containing 95% cyclohexane, 3.33% "Synperonic" NPE 1800 and 1.67% "Tween" 85. Solutions containing "AROTEX" 5C had "AGRAL" 90 added to a final concentration of 0.1%.

As will be seen from the Tables of results below not all the rates shown were used in all the tests.

TABLE V

Height to Top Leaf Ligule in Barley Plants (in Millimeters)

| Rate of Compound No. 6 of Table I applied in grams per hectare (g/ha) | Rate of Chlormequat chloride applied in grams per hectare (g/ha) | |
|---|---|---|
| | 0 (0.1% Agral) | 1000 |
| 0 | 240 (0%) | 203 (15%) |
| 50 | 234 (3%) | 174 (28%) |
| 100 | 233 (3%) | 162 (33%) |
| 500 | 194 (19%) | 117 (51%) |

Figures in brackets are the percentage retardation of height growth of the plants.

TABLE VI

Height to Top Leaf Ligule in Wheat Plants (in Millimeters)

| Rate of Compound No. 6 of Table I applied in grams per hectare (g/ha) | Rate of Chlormequat chloride applied in grams per hectare (g/ha) | |
|---|---|---|
| | 0 (0.1% Agral) | 1000 |
| 0 | 173 (0%) | 106 (39%) |
| 50 | 178 (3%) | 101 (42%) |
| 100 | 173 (0%) | 94 (46%) |
| 500 | 133 (23%) | 71 (59%) |

Figures in brackets are the percentage retardation of height growth of the plants.

The foregoing tables clearly demonstrate the synergism between compound No. 6 of Table I and chlormequat chloride for height retardation only. The tillering data now follows.

TABLE VII

Tiller Number per Plant - Barley Plants

| Rate of Compound No. 6 of Table I applied in grams per hectare | Rate of Chlormequat chloride applied in grams per hectare | | |
|---|---|---|---|
| | 0 | 1000 | 4000 |
| 0 | 2.75 (0%) | 2.90 (+5%) | 3.30 (+20%) |
| 50 | 3.00 (+9%) | | |
| 100 | 2.95 (+7%) | 3.25 (+18%) | 3.70 (+34%) |
| 500 | 2.65 (−4%) | 3.50 (+27%) | 3.55 (+29%) |
| 1000 | 3.00 (+9%) | 3.60 (+31%) | 3.90 (+42%) |

Figures in brackets are percentage (%) difference from the control.

TABLE VIII

Tiller Number per Plant - Wheat Plants

| Rate of Compound No. 6 of Table I applied in grams per hectare | Rate of Chlormequat chloride applied in grams per hectare | | |
|---|---|---|---|
| | 0 | 1000 | 4000 |
| 0 | 3.20 (0%) | 3.50 (+9%) | 4.05 (+27%) |
| 50 | 3.05 (−5%) | 4.50 (+41%) | 4.90 (+53%) |
| 100 | 3.85 (+20%) | 4.85 (+52%) | 4.85 (+52%) |
| 500 | 4.05 (+27%) | 4.70 (+47%) | 5.15 (+61%) |
| 1000 | 3.45 (+8%) | 5.00 (+56%) | 4.85 (+52%) |

Figures in brackets are percentage (%) difference from control.

The results shown in Tables VII and VIII above clearly demonstrate the increased tillering (and the synergistic effect) arising from the use of the mixtures of the test chemical with chlormequat chloride in comparison with the effects achieved when the compounds were used on their own.

EXAMPLE 22

This Example illustrates the ability of Compound No. 6 of Table I to retard the growth of rice plants.

Rice plants were grown in pots, with 2 hills (ie. small clumps) placed in each pot, and were treated with compound No. 6 of Table I at two timings, viz. 14 days after transplanting ($T_1$) and 39 days after transplanting ($T_2$). The compound was applied at 0.1, 0.4, 1.0, 4.0 kg ha$^{-1}$ at 1000 l ha$^{-1}$ using a formulation* system of 5% of the test solution. Final height measurements were made 103 days after transplanting. The results are shown in Table IX below.

TABLE IX

| Treatment | Rate kg ha$^{-1}$ | Percentage reduction in height from base of ear to soil level | |
|---|---|---|---|
| | | T$_1$ | T$_2$ |
| Compound No. 6 of Table I | 0.1 | +5% | +1% |
| Compound No. 6 of Table I | 0.4 | −4% | +4% |
| Compound No. 6 of Table I | 1.0 | −17% | −5% |
| Compound No. 6 of Table I | 4.0 | −66% | −21% |
| Formulation* | 5% | −2% | +5% |

Compound No 6 was formulated as an aqueous emulsifiable concentrate comprising 95% water and 5% of a mixture containing 95% cyclohexane, 3.33% "Synperonic" NPE 1800 and 1.67% "Tween" 85.

The above results clearly demonstrate that the height of the rice plants was reduced by compound No 6 of Table I; and that early application in the growth phase of rice plants produces the greatest stunting effect.

EXAMPLE 23

This Example illustrates the plant growth regulating properties of compound No. 6 of Table I on dicotyledonous plants. Seedlings of apples and vines with approximately 4 to 5 leaves were sprayed at a pressure of 30 p.s.i. (pounds per square inch) to a volume equivalent of 1000 l ha$^{-1}$ with three rates of the test compound formulated as an emulsifiable concentrate. The plants were grown in 10 cm diameter pots containing John Innes No. 1 potting compost and these were maintained in a hot glasshouse at 25° C. day, 20° C. night temperature for a 14 hour day where natural radiation was extended by high pressure mercury vapour lamps (Type MBFR).

Three weeks after treatment, the heights of the seedlings from the soil level to the apical bud were assessed. Results are given in Table X below.

Strong retardation was observed on both apples and vines, particularly at 0.4 and 1.0 kg/ha$^{-1}$.

TABLE X

The Effect of the Test Compound on the height of Apple and Vine Seedlings

| Compound | Rate (ka ha$^{-1}$) | Apples | | Vines | |
|---|---|---|---|---|---|
| | | Height (cm) | % formulation blank | height (cm) | % formulation blank |
| No. 6 of Table I | 0.1 | 12.9 | 78%* | 23.5 | 94% |
| | 0.4 | 10.1 | 61%* | 17.5 | 70%* |
| | 1.0 | 6.0 | 36%* | 17.2 | 69%* |
| Formulation Blank | | 16.5 | | 25.0 | |

*Significantly different from controls at 5% level.

The apple and vine seedlings used in this experiment were grown from pips of Red Delicious (apple) and pips of Ohanez (vine).

EXAMPLE 24

This Example illustrates the plant growth regulating properties of the invention compounds on cereals. Vernalised and chitted seeds of wheat (var. Armada) and barley (var. Sonya) were planted in 10 cm diameter pots containing John Innes Potting Compost No. 2. The compounds were formulated as an emulsifiable concentrate* and sprayed at 30 p.s.i. to a volume equivalent of 1000 liters hectare$^{-1}$ onto 5 replicate pots of barley and wheat containing 3 plants per pot at the 2 leaf stage using a track sprayer. The plants were then arranged in a randomised design and maintained at a minimum night temperature of 11° C. and a minimum day temperature of 14° C. for a 14 hour photo period where natural light addition was extended by high pressure mercury vapor lamps (type MBFR). The plants were subirrigated. The height of top leaf ligule was measured 5 weeks after treatment. The results are shown in Table XI below. These indicate that the compounds caused retardaion and therefore have potential for lodging control in cereals.

*Test Compound 5% Formulation adjuvant+ 95%
+A mixture of 95% cyclohexanone, 3.33% "Synperonic" NPE 1800 and 1.67% "Tween" 85.

TABLE XI

The effects of the Compounds on the height of Barley and Wheat Plants

| Compound No. of Table I | Rate of Application | Barley height to the highest leaf ligule (as a percentage of the control) | Wheat height to highest leaf ligule (as a percentage of the control) |
|---|---|---|---|
| 43 | 4.0 kg ha$^{-1}$ | 77 | 94 |
| 24 | 4.0 kg ha$^{-1}$ | 86 | 65 |
| 6 | 4.0 kg ha$^{-1}$ | 79 | 46 |
| 25 | 4.0 kg ha$^{-1}$ | 74 | 51 |
| 14 | 4.0 kg ha$^{-1}$ | 88 | 65 |

We claim:

1. A compound selected from the group consisting of compounds having the formula (I):

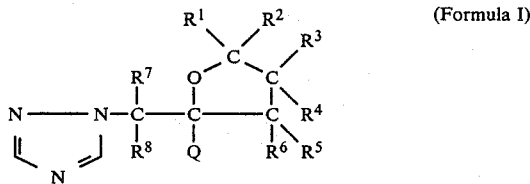

(Formula I)

and stereoisomers thereof, wherein Q is phenyl, halophenyl, C$_{1-4}$ alkylphenyl, C$_{1-4}$ alkoxyphenyl, halo C$_{1-4}$ alkylphenyl, phenylphenyl or phenyl substituted with both halogen and C$_{1-4}$ alkyl groups or phenyl substituted with both halogen and C$_{1-4}$ alkoxy groups; and R$^1$ to R$^6$ and R$^8$, which may be the same or different are H or C$_{1-4}$ alkyl and R$^7$ is H, C$_{1-4}$ alkyl or phenyl; and acid addition salts and metal complexes thereof.

2. A compound according to claim 1 wherein Q is phenyl, 2-, 3- or 4-chlorophenyl, 2,4- or 2,6-dichlorophenyl, 2,4- or 2,6-difluorophenyl, 2-, 3- or 4-fluorophenyl, 2-, 3- or 4-bromophenyl, 2-, 3- or 4-methoxyphenyl, 2,4-dimethoxyphenyl, 2-, 3- or 4-ethoxyphenyl, 2-fluoro-4-chlorophenyl, 2-chloro-4-fluorophenyl, 2-, 3- or 4-methylphenyl, 2-, 3- or 4-ethylphenyl, 2-, 3- or 4-trifluoromethylphenyl, 4-phenylphenyl (4-biphenylyl), 2-chloro-4-methoxyphenyl, 2-fluoro-4-methoxyphenyl, 2-chloro-4-methylphenyl, 2-fluoro-4-methylphenyl, 4-isopropylphenyl, 2-methyl-4-chlorophenyl or 2-methyl-4-fluorophenyl.

3. The compound:
2-(4-chlorophenyl)-2-(1,2,4-triazol-1-yl)methyl-3-prop-1-yltetrahydrofuran;
2-(4-chlorophenyl)-2-(1,2,4-triazol-1-yl)methyl-4-prop-1-yltetrahydrofuran;

2-(4-chlorophenyl)-2-(1,2,4-triazol-1-yl)methyl-3-ethyltetrahydrofuran;
2-(4-chlorophenyl)-2-(1,2,4-triazol-1-yl)methyl-5,5-dimethyltetrahydrofuran;
2-(4-chlorophenyl)-2-(1,2,4-triazol-1-yl)methyl-4-ethyltetrahydrofuran;
2-(4-chlorophenyl)-2-(1,2,4-triazol-1-yl)methyl-4-methyltetrahydrofuran;
2-(4-chlorophenyl)-2-(1,2,4-triazol-1-yl)methyl-3-methyltetrahydrofuran;
2-(2,4-dichlorophenyl)-2-(1,2,4-triazol-1-yl)methyl-4-prop-1-yltetrahydrofuran;
2-(2,4-dichlorophenyl)-2-(1,2,4-triazol-1-yl)methyltetrahydrofuran;
2-(4-chlorophenyl)-2-(1,2,4-triazol-1-yl)methyl-5-methyltetrahydrofuran, diastereomer A;
2-(4-chlorophenyl)-2-(1,2,4-triazol-1-yl)methyl-5-methyltetrahydrofuran, diastereomer B 25);
2-(4-chlorophenyl)-2-(1,2,4-triazol-1-yl)methyl-5-methyl-5-prop-1-yltetrahydrofuran, diastereomer B;
2-(4-chlorophenyl)-2-(1,2,4-triazol-1-yl)methyl-5-methyl-5-but-1-yltetrahydrofuran, diastereomer B;
2-(2-chlorophenyl)-2-(1,2,4-triazol-1-yl)methyl-5-methyltetrahydrofuran, diastereomer A.
2-(2,4-dichlorophenyl)-2-(1,2,4-triazol-1-yl)methyl-5-methyltetrahydrofuran;
2-(4-chlorophenyl)-2-(1,2,4-triazol-1-yl)methyl-4,4-dimethyltetrahydrofuran;
2-(2,4-dichlorophenyl)-2-(1,2,4-triazol-1-yl)methyl-5,5-dimethyltetrahydrofuran;
2-(4-isopropylphenyl)-2-(1,2,4-triazol-1-yl)methyl-5,5-dimethyltetrahydrofuran;
2-(4-methylphenyl)-2-(1,2,4-triazol-1-yl)-methyl-5,5-dimethyltetrahydrofuran; or
2-(4-methoxyphenyl)-2-(1,2,4-triazol-1-yl)methyl-5,5-dimethyltetrahydrofuran.

4. A fungicidal, or plant growth regulating composition comprising an effective amount of a compound of formula (I) as defined in claim 45, and a carrier or diluent.

5. A method of regulating the growth of plants, which comprises applying to the plant, to seed of the plant, or to the locus of the plant or seed, an effective amount of a compound, as defined in claim 1.

6. A method of combating fungal diseases in a plant, which method comprises applying to the plant, to seed of the plant or to the locus of the plant or seed, an effective amount of a compound, as defined in claim 1.

* * * * *